US010506961B1

(12) United States Patent
Schoess

(10) Patent No.: US 10,506,961 B1
(45) Date of Patent: Dec. 17, 2019

(54) DIAGNOSTIC TRANSDUCER AND METHOD

(71) Applicant: Eden Medical, Inc., Howard Lake, MN (US)

(72) Inventor: Jeffrey N. Schoess, Buffalo, MN (US)

(73) Assignee: Eden Medical, Inc., Howard Lake, MN (US)

( * ) Notice: Subject to any disclaimer, the term of this patent is extended or adjusted under 35 U.S.C. 154(b) by 790 days.

(21) Appl. No.: 15/065,810

(22) Filed: Mar. 9, 2016

Related U.S. Application Data

(60) Provisional application No. 62/148,039, filed on Apr. 15, 2015.

(51) Int. Cl.
*A61B 5/1455* (2006.01)
*A61B 5/00* (2006.01)

(52) U.S. Cl.
CPC ........ *A61B 5/14552* (2013.01); *A61B 5/0051* (2013.01)

(58) Field of Classification Search
CPC .. A61B 5/14552; A61B 5/0051; A61B 5/0053
See application file for complete search history.

(56) References Cited

U.S. PATENT DOCUMENTS 4,621,643 A * 11/1986 New, Jr. ............. A61B 5/14552
250/252.1
5,243,544 A 9/1993 Schoess
5,402,777 A 4/1995 Warring et al.
5,549,803 A 8/1996 Schoess et al.
5,642,096 A 6/1997 Leyerer et al.
5,916,179 A 6/1999 Sharrock
(Continued)

OTHER PUBLICATIONS

Armstrong, et al., "Predicting neuropathic ulceration with infrared dermal thermometry", "J Am Podiatr Med Assoc", Jul. 1997, pp. 336-337, vol. 87, No. 7.
(Continued)

*Primary Examiner* — Jacqueline Cheng
*Assistant Examiner* — Abid A Mustansir
(74) *Attorney, Agent, or Firm* — Charles A. Lemaire; Jonathan M. Rixen; Lemaire Patent Law Firm, P.L.L.C.

(57) ABSTRACT

Devices and methods for assessing ulceration risk in a tissue. Some embodiments include a device having a scan head on an extension neck extending from housing and having range of motion relative to the housing. The scan head includes light-emitting system that alternately emits light at different selected wavelengths into the tissue, and a photodetector that generates an electrical signal based on the receive light. A processor calculates regional-perfusion-index (RPI) data based on the electrical signal. Some embodiments provide a tissue-vibration mechanism to help measure mechano-transduction induced recovery from vibratory stimulation for determining short-term metabolic deficit. In some embodiments, the scan head has a topological feature (such as one or more grooves, holes, bumps and/or ridges) that provides pressure-change stimulation for measuring vascular recovery from pressure changes. In some embodiments, the device includes accelerometers and/or pressure sensors to determine where the scan head is positioned relative to the patient's foot.

20 Claims, 21 Drawing Sheets

(56) References Cited

U.S. PATENT DOCUMENTS

| | | | |
|---|---|---|---|
| 5,931,793 A * | 8/1999 | Laudadio | A61B 5/0051 |
| | | | 600/552 |
| 6,014,896 A | 1/2000 | Schoess | |
| 6,090,050 A | 7/2000 | Constantinides | |
| 6,263,737 B1 | 7/2001 | Schoess | |
| 6,398,740 B1 | 6/2002 | Lavery et al. | |
| 6,426,497 B1 | 7/2002 | Martinez et al. | |
| 6,456,567 B1 | 9/2002 | Blevins et al. | |
| 6,544,193 B2 | 4/2003 | Abreu | |
| 6,616,613 B1 | 9/2003 | Goodman | |
| 6,631,288 B1 * | 10/2003 | Bain | A61B 5/0059 |
| | | | 600/476 |
| 6,652,740 B2 | 11/2003 | Schoess | |
| 6,662,647 B2 | 12/2003 | Schoess et al. | |
| 6,718,819 B2 | 4/2004 | Schoess | |
| 6,767,330 B2 | 7/2004 | Lavery et al. | |
| 6,937,885 B1 | 8/2005 | Lewis et al. | |
| 7,003,873 B2 | 2/2006 | Schoess et al. | |
| 8,123,686 B2 | 2/2012 | Fennell et al. | |
| 8,224,425 B2 | 7/2012 | Freeman et al. | |
| 8,320,996 B2 | 11/2012 | Panasyuk et al. | |
| 8,374,682 B2 | 2/2013 | Freeman et al. | |
| 8,525,687 B2 | 9/2013 | Tran | |
| 8,644,911 B1 | 2/2014 | Panasyuk et al. | |
| 8,655,433 B2 | 2/2014 | Freeman et al. | |
| 8,764,651 B2 | 7/2014 | Tran | |
| 8,971,984 B2 | 3/2015 | Freeman et al. | |
| 9,046,085 B2 | 6/2015 | Schoess et al. | |
| 2001/0009265 A1 * | 7/2001 | Schulz | A61B 5/02427 |
| | | | 250/227.14 |
| 2003/0040885 A1 | 2/2003 | Schoess et al. | |
| 2003/0109030 A1 * | 6/2003 | Uchida | A61B 5/14532 |
| | | | 435/287.1 |
| 2009/0234206 A1 * | 9/2009 | Gaspard | A61B 5/0075 |
| | | | 600/322 |
| 2010/0240972 A1 * | 9/2010 | Neal | A61B 5/14552 |
| | | | 600/324 |
| 2010/0324455 A1 | 12/2010 | Rangel et al. | |
| 2013/0018241 A1 * | 1/2013 | Bezzerides | A61B 5/14552 |
| | | | 600/324 |
| 2014/0200486 A1 | 7/2014 | Bechtel et al. | |
| 2014/0275888 A1 * | 9/2014 | Wegerich | A61B 5/6831 |
| | | | 600/324 |

OTHER PUBLICATIONS

Beckert, et al., "The Impact of the Micro-Lightguide O2C for the Quantification of Tissue Ischemia in Diabetic Foot Ulcers.", "Diabetes Care", Dec. 2004, pp. 2863-2867, vol. 27, No. 12.

Cope, Mark, "The application of near infrared spectroscopy to non invasive monitoring of cerebral oxygenation in the newborn infant", "downladed from: http://www.ucl.ac.uk/medphys/research/borl/pub/pub/theses/docs/mcope.pdf", Apr. 1991, Publisher: Thesis submitted for the Degree of Doctor of Philosophy (Ph.D.) of the University of London.

Khaodhiar, et al., "The use of medical hyperspectral technology to evaluate microcirculatory changes in diabetic foot ulcers and predict clinical outcomes", Apr. 2007, pp. 903-910, vol. 30, No. 4.

Sharma, Vikrant, "Near infrared spectroscopy: A study of cerebral hemodynamics during breathholding and development of a system for hotflash measurement", "downloaded from: https://uta-ir.tdl.org/uta-ir/handle/10106/392", Aug. 2005, Publisher: Master's Thesis, University of Texas—Arlington.

Yudovsky, et al., "Hyperspectral Imaging in Diabetic Foot Wound Care", Sep. 2010, p. 1099-1113, vol. 4, No. 5.

Zimny, et al., "Early detection of microcirculatory impairment in diabetic patients with foot at risk", Oct. 2001, pp. 1810-1814, vol. 24, No. 10.

\* cited by examiner

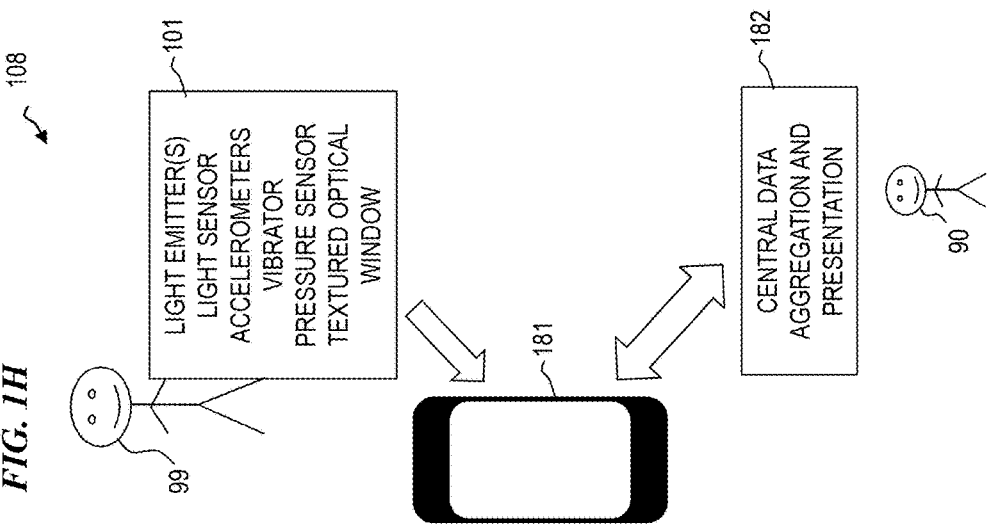
FIG. 1H
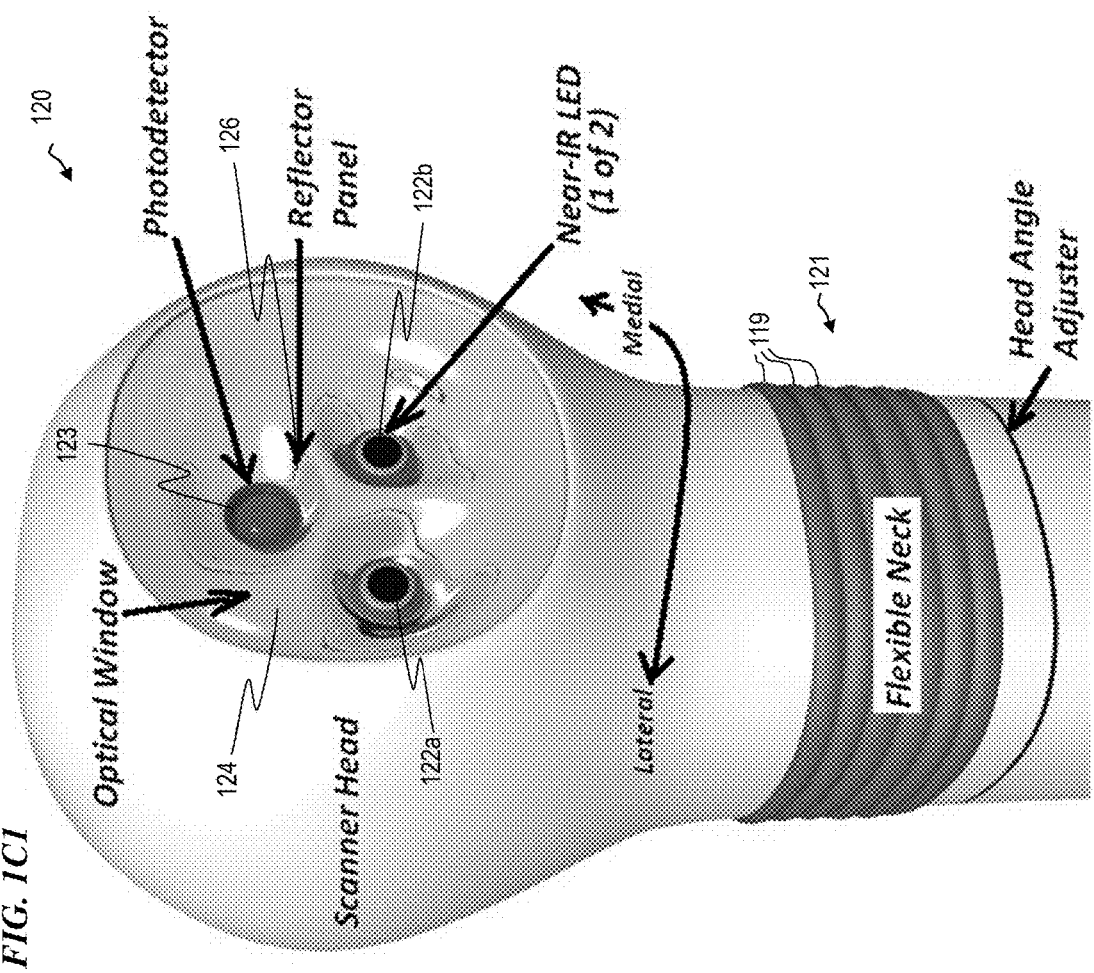
FIG. 1C1

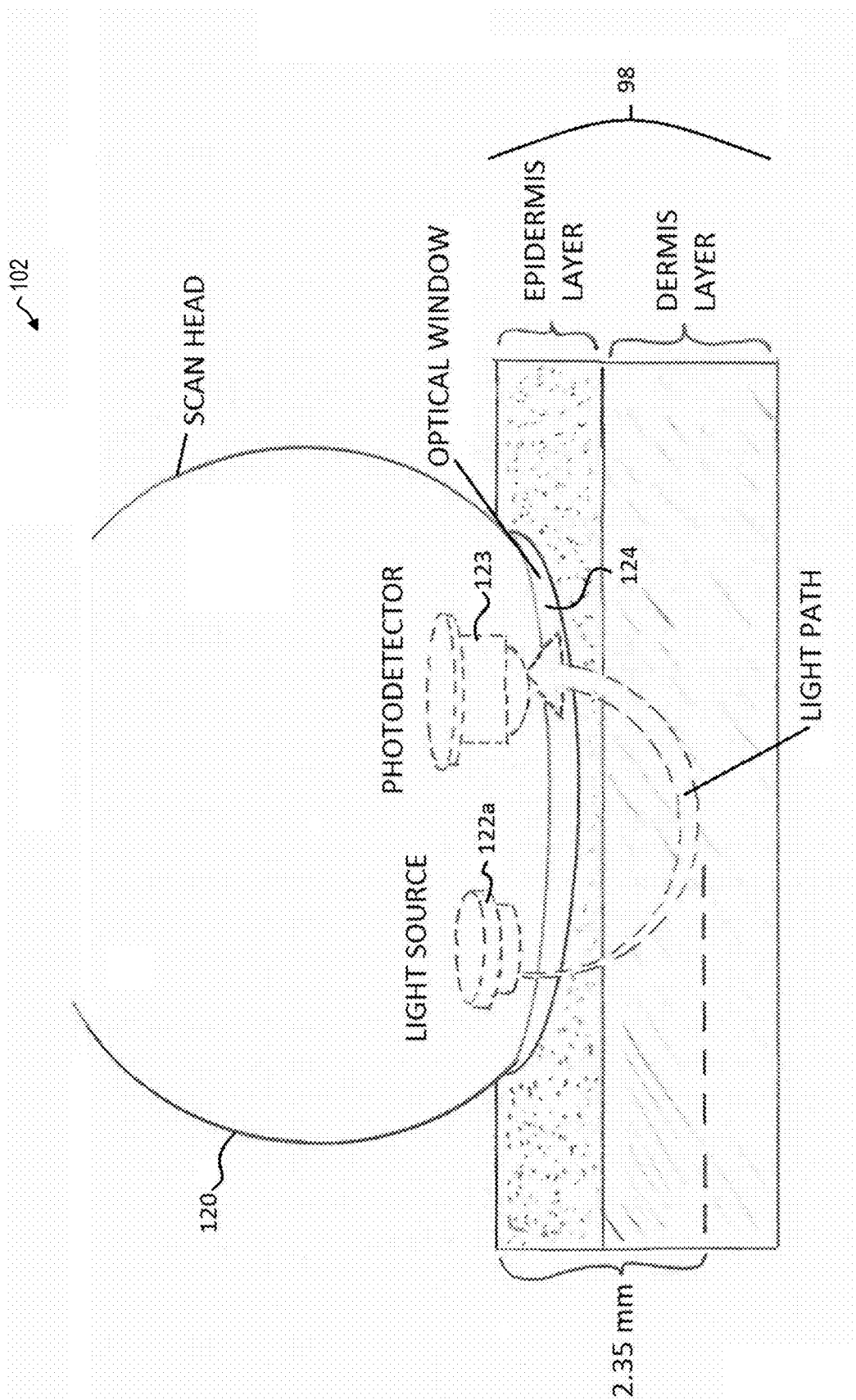
FIG. 1C2

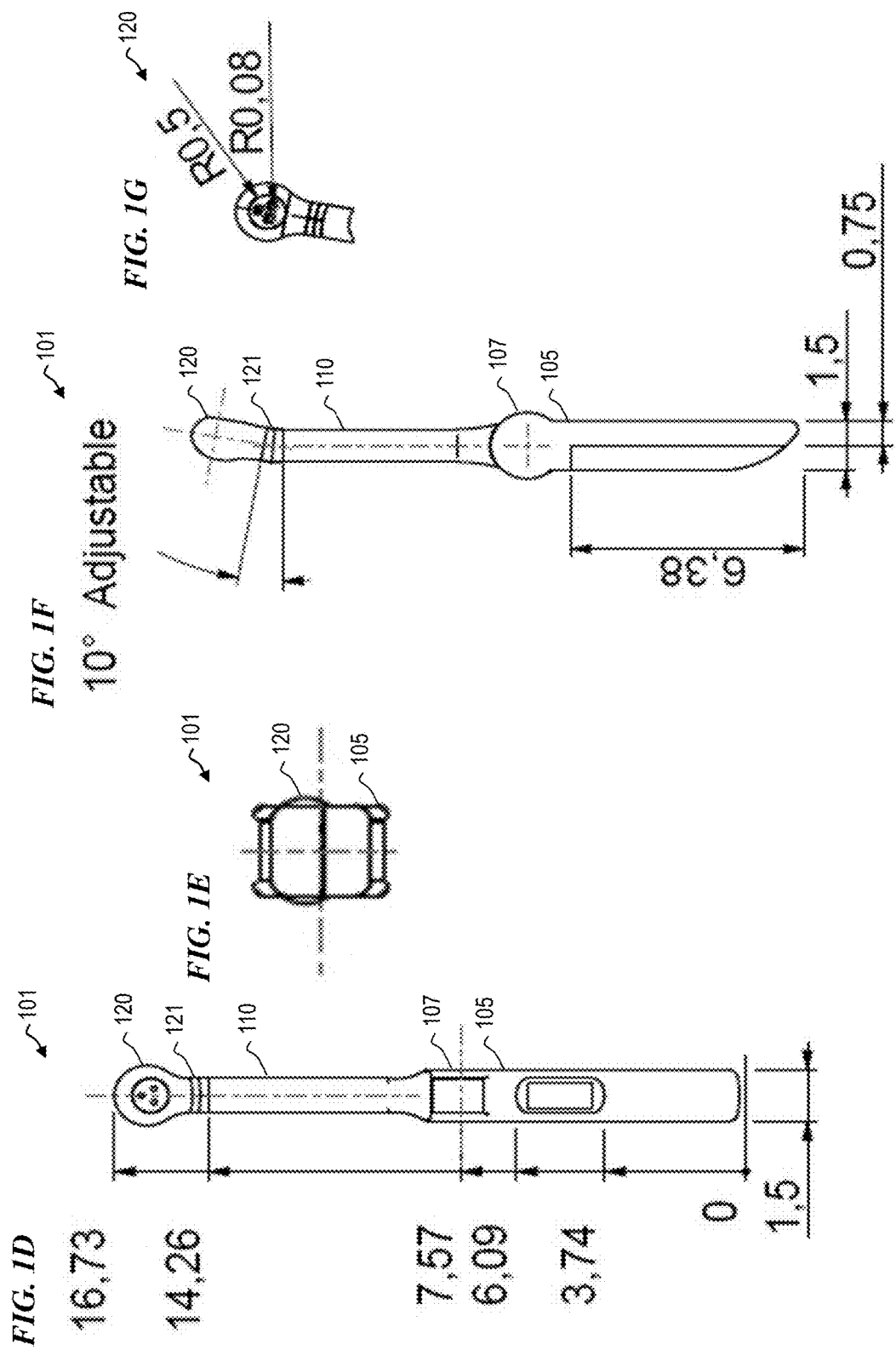

DIAGNOSTIC TRANSDUCER AND METHOD

CROSS-REFERENCE TO RELATED APPLICATION

This application claims priority benefit, under 35 U.S.C. § 119(e), of U.S. Provisional Patent Application No. 62/148,039, filed Apr. 15, 2015 by Jeffrey N. Schoess, titled "Diagnostic transducer and method," which is incorporated herein by reference in its entirety.

STATEMENT REGARDING FEDERALLY SPONSORED RESEARCH OR DEVELOPMENT

Research and development of the concepts disclosed herein were funded in part by grants from the National Institutes of Health, Grant No. 1R43DK083782-01. The United States Government may have certain rights in the claimed invention.

FIELD OF THE INVENTION

The present invention relates to devices and methods to assess tissue ulceration, and in particular, to a diagnostic transducer and method for evaluating perfusion impairment in the foot and other body tissue of a human patient, wherein some embodiments include automatic transmission of evaluation data to a central facility for assessment by a health-care professional, as well as for aggregation and analysis of similar data from a large population of patients.

BACKGROUND OF THE INVENTION

Diabetic foot ulceration is a major complication of diabetes and afflicts as many as 15 to 25% of type 1 and type 2 diabetes patients during their lifetime. If untreated, diabetic foot ulcers may become infected and require total or partial amputation of the affected limb. Early identification of tissue at risk of ulcerating could enable proper preventive care, thereby reducing the incidence of foot ulceration. Furthermore, noninvasive assessment of tissue viability around already formed ulcers could inform the diabetes caregiver about the severity of the wound and help assess the need for amputation. Hyperspectral imaging can be used to assess the risk of diabetic foot ulcer development, producing a map of oxyhemoglobin and deoxyhemoglobin concentrations in the dermis of the foot. An oximetry-based ulcer-formation prediction index can be used in conjunction with estimates of epidermal thickness to eliminate false positives. Unfortunately, in vivo hyperspectral imaging systems are not suitable for mobile health use (nursing and home care), are very expensive, awkward, and require specialized clinical operator training. (See *Hyperspectral Imaging in Diabetic Foot Care*, by Dimitry Yudovsky, published by Journal of Diabetes Science and Technology, Vol. 4, Issue 5, 2010.)

Various sensors and/or transducers are described by the inventor of the present invention (in some cases with co-inventors) in U.S. Pat. Nos. 5,243,544; 5,549,803; 6,014,896; 6,263,737; 6,426,497; 6,456,567; 6,652,740; 6,662,647; 6,718,819; 7,003,873; and 9,046,085, each of which is incorporated herein by reference. U.S. Patent Application Publication 2003/0040885 is also incorporated herein by reference.

U.S. Pat. No. 5,402,777 to Warring et al. issued on Apr. 4, 1995 with the title "Methods and devices for facilitated non-invasive oxygen monitoring" and is incorporated herein by reference. U.S. Pat. No. 5,402,777 describes a sensor system for use with a blood characteristic measurement device such as a pulse oximeter, on areas of the body having low normal cutaneous blood flow and for monitoring a blood characteristic such as oxygen saturation and pulse rate of patients, preferably over an extended period of time. The sensor system includes (a) a transdermal device containing a blood perfusion-enhancing agent that is administered in a controlled amount to the skin of a human patient and (b) a skin surface sensor.

U.S. Pat. No. 5,642,096 to Leyerer et al. issued on Jun. 24, 1997 with the title "Device for prevention of ulcers in the feet of diabetes patients" and is incorporated herein by reference. U.S. Pat. No. 5,642,096 describes a device for prevention of ulcers in the feet of diabetes patients embodied in a footwear article such as in a shoe. The device includes a sensor disposed in a contained liquid mass of a hydrocell carried in the shoe inner sole, the sensor being one that detects both pressure and temperature values to which the patient's feet are exposed. The sensor includes a bridge circuit comprised of four piezoresistors arranged in two diagonally arrayed pairs, the resistance of one pair of resistors increasing and the resistance of the second pair decreasing in the presence of an increase in the pressure condition in the hydrocell, the resistance of all the resistors increasing or decreasing responsive to respective increases and decreases of temperature in the hydrocell. Outputs from the bridge circuit denotive of respective pressure and temperature values are acquired by a warning signal generator to operate same to generate a patient discernible warning signal that indicates to the patient a need to take action to avoid continuance of exposure to the condition. A grid array sensor detects localized pressure changes on the bottom of the foot by reducing the resistance between conductors present at the location of the increases pressure. The decreased resistance causes an increase in current flow between the conductors which is detected by a processor which in turn provides an indication of the increased pressure condition.

U.S. Pat. No. 5,916,179 to Sharrock issued on Jun. 29, 1999 with the title "System and method for reducing iatrogenic damage to nerves" and is incorporated herein by reference. U.S. Pat. No. 5,916,179 describes a method for predicting peripheral nerve damage comprising the steps of placing a pressure transducer on the skin of a patient proximate to a peripheral nerve; measuring the pressure with the pressure transducer over time; and estimating a damage to the nerve based on the pressure and duration of application and a nerve damage model.

U.S. Pat. No. 6,090,050 to Constantinides issued on Jul. 18, 2000 with the title "Thermometric apparatus and method" and is incorporated herein by reference. U.S. Pat. No. 6,090,050 describes a thermometric apparatus useful for recording temperatures, after sensing contact with, or proximity to, a dermal surface is disclosed. The apparatus also provides various visual and aural mechanisms for indicating alarm conditions to the user. A method for thermometric diagnosis using temperatures acquired from bilateral dermal surfaces is also disclosed. The apparatus and method are especially useful in the early diagnosis of plantar foot surface pre-ulceration conditions which may be present in diabetic persons.

U.S. Pat. No. 6,398,740 to Lavery et al. issued on Jun. 4, 2002 with the title "Apparatus and method for monitoring the temperatures on the plantar aspects of a human foot and other vital health information" and is incorporated herein by reference. U.S. Pat. No. 6,398,740 describes an apparatus and method for monitoring items of vital health information including temperature of the plantar aspects of the foot of the human, body weight, blood pressure, pulse rate, blood glucose level and blood oxygen level. The apparatus includes a platform on which the user stands. Included on the platform are a set of heat sensitive signal generating devices. The temperature at predetermined locations on the plantar aspects of the human foot are determined by the signals obtained from the individual heat sensitive, signal generating probes. Other items of vital health information may be obtained by other sensors on the apparatus.

U.S. Pat. No. 6,544,193 to Abreu issued on Apr. 8, 2003 with the title "Noninvasive measurement of chemical substances" and is incorporated herein by reference. U.S. Pat. No. 6,544,193 describes utilization of a contact device placed on the eye in order to detect physical and chemical parameters of the body as well as the non-invasive delivery of compounds according to these physical and chemical parameters, with signals being transmitted continuously as electromagnetic waves, radio waves, infrared and the like. One of the parameters to be detected includes non-invasive blood analysis utilizing chemical changes and chemical products that are found in the conjunctiva and in the tear film. A transensor mounted in the contact device laying on the cornea or the surface of the eye is capable of evaluating and measuring physical and chemical parameters in the eye including non-invasive blood analysis. The system utilizes eye lid motion and/or closure of the eye lid to activate a microminiature radio frequency sensitive transensor mounted in the contact device. The signal can be communicated by wires or radio telemetered to an externally placed receiver. The signal can then be processed, analyzed and stored. Several parameters can be detected including a complete non-invasive analysis of blood components, measurement of systemic and ocular blood flow, measurement of heart rate and respiratory rate, tracking operations, detection of ovulation, detection of radiation and drug effects, diagnosis of ocular and systemic disorders and the like.

U.S. Pat. No. 6,616,613 to Goodman issued on Sep. 9, 2003 with the title "Physiological signal monitoring system" and is incorporated herein by reference. U.S. Pat. No. 6,616,613 describes a health monitoring and biofeedback system comprising a photoplethysmography (PPG) sensor, a processing device, and a Web site server for determining, displaying and analyzing various cardiovascular parameters. The PPG sensor is installed within a manually operated user input device such as a mouse or keyboard, measures a user's blood volume contour and transmits it to a processing device such as a personal computer or a personal digital assistant (PDA). The system determines a plurality of cardiovascular indices including mean blood pressure, heart rate, body temperature, respiratory rate, and arterial compliance on the basis of signal characteristics of the systolic wave pulse and the systolic reflected wave pulse present within the digital volume pulse derived from the PPG pulse contour. Signal characteristics of the systolic reflected wave pulse can be determined through various pulse analysis techniques including derivative analysis of the digital volume pulse signal, bandpass filtering or respiratory matrix frequency extraction techniques. By subtracting the systolic reflected wave pulse contour from the digital volume pulse contour, characteristics of the systolic wave pulse can also be identified. The system also provides for the accurate determination of systolic and diastolic blood pressure by using a non-invasive blood pressure monitor to calibrate the relationships between arterial or digital blood pressure and characteristics of the user's digital volume pulse contour. In this way, a wide variety of cardiovascular and respiratory data can be obtained. The system also facilitates the transmittal of such data to the system web site for further analysis, storage, and retrieval purposes.

U.S. Pat. No. 6,767,330 to Lavery et al. issued on Jul. 27, 2004 with the title "Foot temperature and health monitoring system" and is incorporated herein by reference. U.S. Pat. No. 6,767,330 describes an apparatus and method for monitoring skin temperatures at predetermined locations on the body of a human or an animal. One embodiment includes a platform with a grid including holes on which the user stands. Under the grid is a movable array of light sensors and temperature sensors. The foot position is determined from the output of the light sensors. The temperatures at predetermined locations on the skin surface are determined by the signals obtained from the temperature sensors. Additional vital health information may be obtained by other sensors on the apparatus. The data may be stored for future retrieval, or transmitted to a remote location for off-site monitoring. Alternative embodiments include sensor blankets or wraps whereby temperature sensors monitor skin temperature for areas of pressure on the blanket or areas covered by the wrap.

U.S. Pat. No. 6,937,885 to Lewis et al. issued on Aug. 30, 2005 with the title "Multispectral/hyperspectral medical instrument" and is incorporated herein by reference. U.S. Pat. No. 6,937,885 describes a medical instrument that comprises: a first-stage optic responsive to a tissue surface of a patient; a spectral separator optically responsive to the first stage optic and having a control input; an imaging sensor optically responsive to the spectral separator and having an image data output; and a diagnostic processor having an image acquisition interface with an input responsive to the imaging sensor and a filter control interface having a control output provided to the control input of the spectral separator.

U.S. Pat. No. 8,123,686 to Fennell et al. issued on Feb. 28, 2012 with the title "Method and apparatus for providing rolling data in communication systems" and is incorporated herein by reference. U.S. Pat. No. 8,123,686 describes methods and systems for providing data communication in medical systems.

U.S. Pat. No. 8,224,425 to Freeman et al. issued on Jul. 17, 2012 with the title "Hyperspectral imaging in diabetes and peripheral vascular disease" and is incorporated herein by reference. U.S. Pat. No. 8,224,425 describes methods and systems of hyperspectral and multispectral imaging of medical tissues. In particular, the invention is directed to new devices, tools and processes for the detection and evaluation of diseases and disorders such as, but not limited to diabetes and peripheral vascular disease, that incorporate hyperspectral or multispectral imaging.

U.S. Pat. No. 8,320,996 to Panasyuk et al. issued on Nov. 27, 2012 with the title "Medical hyperspectral imaging for evaluation of tissue and tumor" and is incorporated herein by reference. U.S. Pat. No. 8,320,996 describes apparatus and methods for hyperspectral imaging analysis that assists in real and near-real time assessment of biological tissue condition, viability, and type, and monitoring the above over time. Embodiments of the invention are particularly useful in surgery, clinical procedures, tissue assessment, diagnostic procedures, health monitoring, and medical evaluations, especially in the detection and treatment of cancer.

U.S. Pat. No. 8,374,682 to Freeman et al. issued on Feb. 12, 2013 with the title "Hyperspectral imaging in diabetes and peripheral vascular disease" and is incorporated herein by reference. U.S. Pat. No. 8,374,682 describes methods and systems of hyperspectral and multispectral imaging of medical tissues. In particular, the invention is directed to new devices, tools and processes for the detection and evaluation of diseases and disorders such as, but not limited to diabetes and peripheral vascular disease, that incorporate hyperspectral or multispectral imaging.

U.S. Pat. No. 8,525,687 to Tran issued on Sep. 3, 2013 with the title "Personal emergency response (PER) system" and is incorporated herein by reference. U.S. Pat. No. 8,525,687 describes systems and methods for identifying an activity of an object including identifying each elemental motion of a sequence of elemental motions of a device attached to the object; and identifying the activity of the object, comprising matching the sequence of identified elemental motions of the device with a library of stored sequences of elemental motions, wherein each stored sequence of elemental motions corresponds with an activity.

U.S. Pat. No. 8,644,911 to Panasyuk et al. issued on Feb. 4, 2014 with the title "OxyVu-1 hyperspectral tissue oxygenation (HTO) measurement system" and is incorporated herein by reference. U.S. Pat. No. 8,644,911 describes a hyperspectral/multispectral system referred to as the OxyVu-1 system. The hyperspectral imaging technology performs spectral analysis at each point in a two-dimensional scanned area producing an image displaying information derived from the analysis. For the OxyVu-1 system, the spectral analytical methods determined in superficial tissues approximate values of oxygen saturation (HT-Sat), oxyhemoglobin levels (HT-oxy), and deoxyhemoglobin levels (HT-deoxy). The OxyVu-1 system displays the tissue oxygenation in a two-dimensional, color-coded image. The system contains a system console, a cart, system electronics, CPU, monitor, keyboard, pointing device and printer. The hyperspectral instrument head with support arm contains broadband illuminator, camera and spectral filter for collecting hyperspectral imaging cube. The single use OxyVu Check Pads and Targets are used to perform an instrument check prior to patient measurements. The OxyVu Target is placed within the intended field of view and is used as a fiduciary mark for image registration and for focusing.

U.S. Pat. No. 8,655,433 to Freeman et al. issued on Feb. 18, 2014 with the title "Hyperspectral imaging in diabetes and peripheral vascular disease" and is incorporated herein by reference. U.S. Pat. No. 8,655,433 describes methods and systems of hyperspectral and multispectral imaging of medical tissues. In particular, the invention is directed to new devices, tools and processes for the detection and evaluation of diseases and disorders such as, but not limited to diabetes and peripheral vascular disease, that incorporate hyperspectral or multispectral imaging.

U.S. Pat. No. 8,764,651 to Tran issued on Jul. 1, 2014 with the title "Fitness monitoring" and is incorporated herein by reference. U.S. Pat. No. 8,764,651 describes a heart monitoring system for a user includes a body wearable appliance placed on or near the user skin and having one or more sensors to capture fitness data and a wireless transceiver to communicate fitness data; and a processor coupled to the wireless transceiver to receive fitness data.

U.S. Pat. No. 8,971,984 to Freeman et al. issued on Mar. 3, 2015 with the title "Hyperspectral technology for assessing and treating diabetic foot and tissue disease" and is incorporated herein by reference. U.S. Pat. No. 8,971,984 describes an index map comprising both pressure and perfusion information from a diabetic patient foot for the purpose of treatment. The index map may also be a map of perfusion and/or metabolism of the tissue (reflecting oxygen delivery and oxygen extraction), obtained by thermal imaging, hyperspectral imaging, or duplex ultrasound, MRA, CT or laser Doppler imaging. This information aids treatment in prevention of diabetic foot ulceration and amputation and in treatment of tissue compromise to prevent tissue loss in other body regions.

United States Patent Application Publication 2010/0324455 of Rangel et al. published on Dec. 23, 2010 with the title "Devices for management of foot injuries and methods of use and manufacture thereof" and is incorporated herein by reference. Patent Application Publication 2010/0324455 describes orthotic devices for use in managing the treatment and prevention of lower extremity injuries, including foot ulcers. In various aspects, the present invention provides foot-worn orthotics which provide for improved compliance monitoring, and methods of their manufacture and use.

United States Patent Application Publication 2014/0200486 of Bechtel et al. published on Jul. 17, 2014 with the title "System and method for continuous monitoring of a human foot for signs of ulcer development" and is incorporated herein by reference. Patent Application Publication 2014/0200486 describes a system and method for monitoring a human foot by measuring pressures applied to regions of the foot or by measuring another tissue-health related condition. A light source in the 400 nm to 1400 nm range and a detector can be embedded in a wearable article that contacts tissue while in use, spaced 200 µm to 1 cm apart, and measure a tissue hemoglobin condition. A pressure-sensing array may be read by a low-power control circuit, and a power source can be incorporated in the article. An external processing unit wirelessly coupled to the control circuit can relate pressures measured with counts that are associated with injury risk, and an alert system can notify a patient if the counts exceed a predetermined threshold. A relationship between pressure experienced by a region of tissue and the risk of ulcer development in that region may be derived.

The following references are incorporated herein by reference for all purposes: Sharma V., "Near infrared spectroscopy: A study of cerebral hemodynamics during breathholding and development of a system for hotflash measurement," Master's Thesis, University of Texas-Arlington, 2005, and Cope M., "The application of near infrared spectroscopy to non invasive monitoring of cerebral oxygenation in the newborn infant," Ph.D. Thesis, University College London, 1991.

There remains a need for improved systems and methods to assess tissue ulceration.

SUMMARY OF THE INVENTION

The present invention provides an apparatus, system and method for interactive home assessment of a medical condition by a patient. Some embodiments of the apparatus include a handheld device that has an optical sensor that quantifies perfusion impairment of the patient's foot, facilitating clinical management through early detection, as well as prevention of, diabetic foot ulcers. In some embodiments, the handheld device includes an optical window having a shaped surface topology that, when pressed against and/or "rolled" (i.e., moved in a sliding motion) across the skin, causes changes in blood perfusion that are measured at a plurality of locations on the foot by moving the scan head on the foot while optical emitters in the device emit light of various wavelengths and the optical sensor senses diffused and/or specular return of the light. The optical sensor generates a signal that is analyzed by the system (in some embodiments, much of the analysis is performed in the handheld device and presented on a display on the device, while other embodiments perform analysis in the smartphone and or in a central computer server). In some embodiments, the handheld device communicates (in some embodiments, wirelessly) with the patient's smartphone, which in turn communicates with a computer system at a hospital or other health-care facility, where data collected by the handheld device is aggregated and presented to a health-care professional for assessment. In some embodiments, some amount of analysis and formatting of the data are performed in the handheld device, in the smartphone and in the health-care facility's computer system. In some embodiments, a plurality of such health-care facility computer systems communicate with a central server that collects, analyzes, and distributes demographic data for various populations of patients.

In some embodiments, the present invention provides information about dermal vascularity and tissue-perfusion phenomena diagnostics.

BRIEF DESCRIPTION OF THE FIGURES

FIG. 1C1 is a perspective schematic diagram of scan head 120, according to some embodiments of the present invention.

FIG. 1C2 is a schematic diagram 102 showing scan head 120 being used to assess tissue 98, according to some embodiments of the present invention.

FIG. 1D is a front-view schematic diagram of transducer 101, according to some embodiments of the present invention.

FIG. 1E is a top-view schematic diagram of transducer 101, according to some embodiments of the present invention.

FIG. 1F is a side-view schematic diagram of transducer 101, according to some embodiments of the present invention.

FIG. 1G is a front-view schematic diagram of scan head 120, according to some embodiments of the present invention.

FIG. 1H is a block diagram of a process 108 for assessing ulceration risk in a tissue.

FIG. 2 is a schematic diagram 201 of a mechano-transduction-enhanced transducer 201 that creates a mechano-stress effect for a tissue.

DETAILED DESCRIPTION OF THE INVENTION

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Figure 1B:
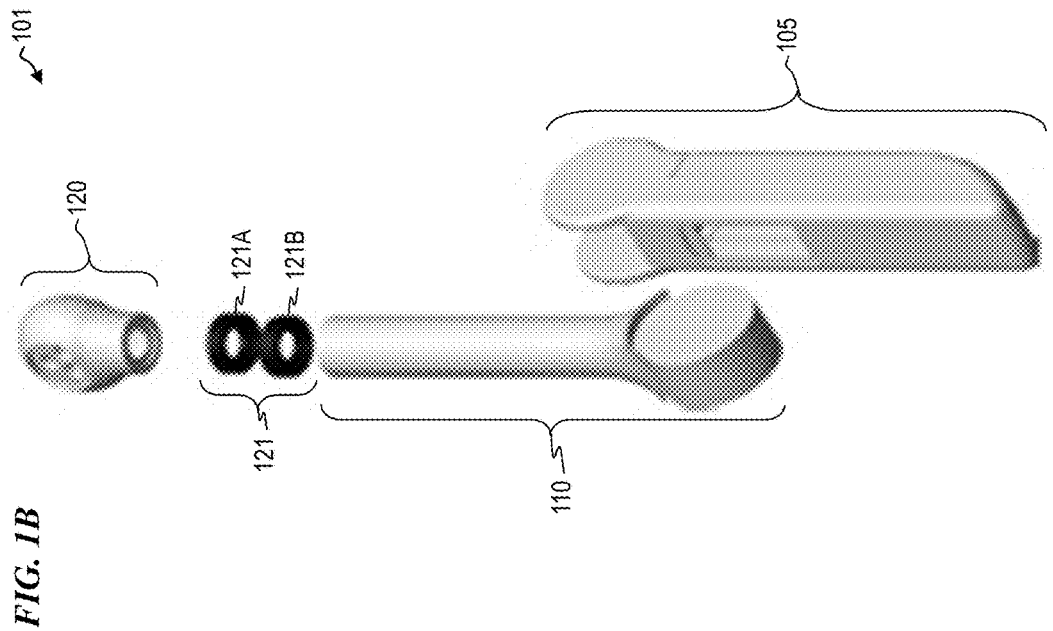
FIG. 1B is an exploded-view schematic diagram of transducer 101, according to some embodiments of the present invention.
Figure 1A:
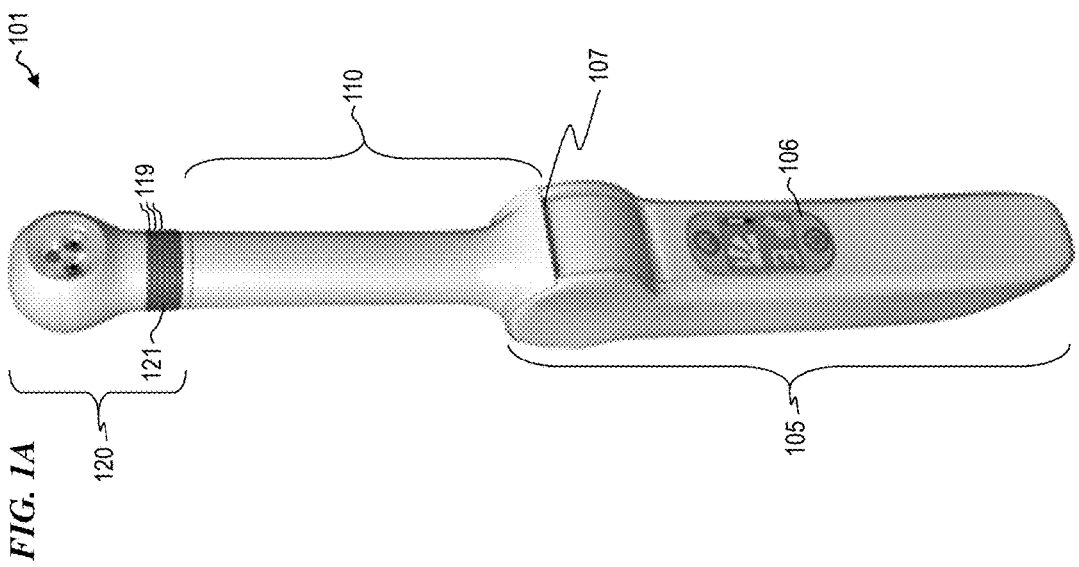
FIG. 1A is a perspective schematic diagram of a diagnostic transducer 101, according to some embodiments of the present invention.

FIG. 1A is a perspective schematic diagram of a diagnostic transducer 101, according to some embodiments of the present invention. In some embodiments, transducer 101 provides in vivo real-time monitoring for ulceration assessment of the diabetic foot. In some embodiments, transducer 101 is referred to herein as FIRST (Foot Infrared Rolling-Scan Transducer). In some embodiments, transducer 101 performs near-infrared spectral imaging to quantify the levels of deoxygenated hemoglobin (deoxyhemoglobin; also called deoxy-Hb) and oxygenated hemoglobin (oxyhemoglobin; also called oxy-Hb) related to cutaneous perfusion related to metabolic parameters such as edema, erythema, and microcirculation loss. In some embodiments, transducer 101 is a hand-held device and is used during daily foot self-exams to encourage diabetic patients to see their doctor at the "first sign" of a potential ulceration problem related to repetitive stress during activities of daily living. In some embodiments, transducer 101 performs in vivo monitoring as a multi-wavelength measurement that assesses changes in absorption of deoxy-Hb and oxy-Hb in foot tissue.

In some embodiments, transducer 101 includes a hand-held housing 105, an extension neck 110, and a scan head 120. In some embodiments, housing 105 includes a user interface panel 106. In some embodiments, transducer 101 includes a flexible joint 121 between extension neck 110 and scan head 120, wherein the flexible joint 121 provides for maximum contact between scan head 120 and the tissue (e.g., foot tissue) being analyzed (in some such embodiments, flexible joint 121 provides a range of bending motion between scan head 120, and extension neck 110 of approximately ten (10) degrees). In some embodiments, flexible joint 121 also provides a range of rotational motion between scan head 120 and extension neck 110. In some embodiments, transducer 101 includes an articulated joint 107 between housing 105 and extension neck 110. In some embodiments, one or more portions of transducer 101 are fabricated via three-dimensional (3D) printing (e.g., in some embodiments, stereolithography (SLA) 3D printing, Polyjet 3D printing, or the like).

In some embodiments, the present invention uses the following method of Calculating oxyhemoglobin and deoxyhemoglobin. In some embodiments, the foot infrared rolling scan transducer 101 measures oxyhemoglobin and deoxyhemoglobin by emitting, successively, each one of a plurality of wavelengths (multi-wavelength) of light. For each such emission, the light propagates through foot tissue and is detected by the photodetector 123 (See FIG. 1C1) is converted into an equivalent electrical signal. This electrical signal is low-pass filtered (using either analog circuitry before it is converted from analog to digital (ADC), or using hardware and/or software to digitally low-pass-filter the digital signal after the signal is digitized) to remove any human-motion artifacts. In some embodiments, the signal is digitized into an equivalent 12-bit word (or, in other embodiments, other suitable resolution) for data analysis and converted into units of oxyhemoglobin ($HbO_2$) and deoxyhemoglobin (Hb). The equations Eq. 1 and Eq. 2 used by some embodiments define the expression of oxyhemoglobin and deoxyhemoglobin referencing the work of Sharma (Sharma V., "Near infrared spectroscopy: A study of cerebral hemodynamics during breathholding and development of a system for hotflash measurement," Master's Thesis, University of Texas-Arlington, 2005; which is incorporated herein by reference). The intensity of light during stimulus refers to the light detected by the photodetector during patient testing. The intensity of light during baseline refers to the time period when no light is transmitted (i.e. both LEDs are off).

$$\Delta HbO_2 = \frac{\log\frac{I^b(\lambda_{730nm})}{I^s(\lambda_{730nm})}\varepsilon_{deoxy}(\lambda_{850nm}) - \log\frac{I^b(\lambda_{850nm})}{I^s(\lambda_{850nm})}\varepsilon_{deoxy}(\lambda_{730nm})}{L[\varepsilon_{oxy}(\lambda_{730nm})\varepsilon_{deoxy}(\lambda_{850nm}) - \varepsilon_{oxy}(\lambda_{850nm})\varepsilon_{deoxy}(\lambda_{730nm})]} \quad \{Eq. 1\}$$

$$\Delta Hb = \frac{\log\frac{I^b(\lambda_{850nm})}{I^s(\lambda_{850nm})}\varepsilon_{oxy}(\lambda_{730nm}) - \log\frac{I^b(\lambda_{730nm})}{I^s(\lambda_{730nm})}\varepsilon_{oxy}(\lambda_{850nm})}{L[\varepsilon_{oxy}(\lambda_{730nm})\varepsilon_{deoxy}(\lambda_{850nm}) - \varepsilon_{oxy}(\lambda_{850nm})\varepsilon_{deoxy}(\lambda_{730nm})]} \quad \{Eq. 2\}$$

where
$\lambda HbO_2 \rightarrow$ change in oxy hemoglobin concentration,
$\lambda Hb \rightarrow$ change in deoxy hemoglobin concentration,
$\Delta Hb_{total} \rightarrow$ change in total hemoglobin concentration,
$I^s(\lambda_x) \rightarrow$ intensity of light at wavelength 'x' during stimulus,
$I^b(\lambda_x) \rightarrow$ intensity of light at wavelength 'x' during baseline,
$\varepsilon_{oxy}(\lambda_x) \rightarrow$ extinction coefficient for oxy-hemoglobin at wavelength 'x',
$\varepsilon_{deoxy}(\lambda_x) \rightarrow$ extinction coefficient for deoxy-hemoglobin at wavelength 'x',
$L \rightarrow$ optical length.

In some embodiments, the extinction coefficients for oxyhemoglobin and deoxyhemoglobin at 730 and 850 nm are obtained using teaching from the dissertation work of Mark Cope (Cope M., "The application of near infrared spectroscopy to non invasive monitoring of cerebral oxygenation in the newborn infant," Ph.D. Thesis, University College London, 1991) for human blood (see page 215, FIG. 6.1 of Cope). The typical values used for extinction coefficients are:

$\varepsilon_{oxy}(\lambda_{730}) = 0.4383$ nM$^{-1}$cm$^{-1}$   $\varepsilon_{deoxy}(\lambda_{730}) = 1.3029$ nM$^{-1}$cm$^{-1}$
$\varepsilon_{oxy}(\lambda_{850}) = 1.1596$ nM$^{-1}$cm$^{-1}$   $\varepsilon_{deoxy}(\lambda_{850}) = 0.7861$ nM$^{-1}$cm$^{-1}$ Substituting in the values of the extinction coefficients into Eq. 1 and Eq. 2, one gets:

$$\Delta HbO_2 = \left[-0.6740\log\left(\frac{I^b(\lambda_{850nm})}{I^s(\lambda_{850nm})}\right) + 1.1171\log\left(\frac{I^b(\lambda_{730nm})}{I^s(\lambda_{730nm})}\right)\right]\bigg/L$$

$$\Delta Hb = \left[-0.3758\log\left(\frac{I^b(\lambda_{850nm})}{I^s(\lambda_{850nm})}\right) + 0.9943\log\left(\frac{I^b(\lambda_{730nm})}{I^s(\lambda_{730nm})}\right)\right]\bigg/L$$

FIG. 1B is an exploded-view schematic diagram of transducer 101, according to some embodiments of the present invention. Referring to FIG. 1A, FIG. 1B and FIG. 1C, the transducer 101 includes several key components—the scan head 120, the flexible joint 121, the extension neck 110, and the transducer housing 105. In some embodiments, the scan head 120, as shown in FIG. 1C1, includes two or more near-infrared LED light sources of different wavelength 122a and 122b, a photodetector 123, and reflector panel 126. In some embodiments, the flexible neck 121 includes two ring segments 121A and 121B stacked on top of each other. In some embodiments, each ring segment 121A and 121B includes a plurality of flexible ribs 119 to promote bending of the scan head 120. In some embodiments, the ring segments 121A and 121B are fabricated via silicon molding. The extension neck 110 fits into the housing 105 to form articulated joint 107 (see FIG. 1A) to allow the user to perform single-axis rotation of the scan head 120, in order that head 120 of diagnostic transducer 101, for example, may be positioned to act on the side of the foot (when straight) or around the corner to the bottom of the foot (when bent at a 90-degree angle).

FIG. 1C1 is a perspective schematic diagram of scan head 120, according to some embodiments of the present invention. In some embodiments, scan head 120 includes a pair of light sources 122a and 122b (e.g., in some embodiments, light sources 122a and 122b are each a near infrared (Near-IR) light-emitting diode (LED)). In some embodiments, scan head 120 further includes a photodetector 123. In some embodiments, scan head 120 further includes an optical window 124, (in some embodiments, window 124, which is transparent to the wavelengths from the plurality of light sources 122a-122b, covers the area of scan head 120 from which light emitted from light sources 122a and 122b is projected toward target tissue, and through which returning light from target tissue is detected by photodetector 123). In some embodiments, light sources 122a and/or 122b emit light that is transmitted through optical window 124 and into the tissue to be analyzed, and photodetector 123 receives the light that has passed back through optical window 124 after it has interacted with the tissue. In some embodiments, the outer circumference or rim of optical window 124 includes an opaque light-proof covering to prevent stray light from entering optical window 124 during use (in some such embodiments, the rim is a threaded metal ring that allows optical window 124 to be removably screwed onto scan head 120). (In some embodiments, the two LEDs 122a and 122b and the photodetector 123 each have a small, individual reflector panel surrounding them.) In some embodiments, scan head 120 is located at the end of extension neck 110 in order to provide extended reach to measure foot surface skin condition. In some embodiments, user interface panel 106 includes an organic Light Emitting Diode (OLED) display to adjust the optical power setting, display remaining battery life, and display regional perfusion index (RPI) data.

Figure 2:
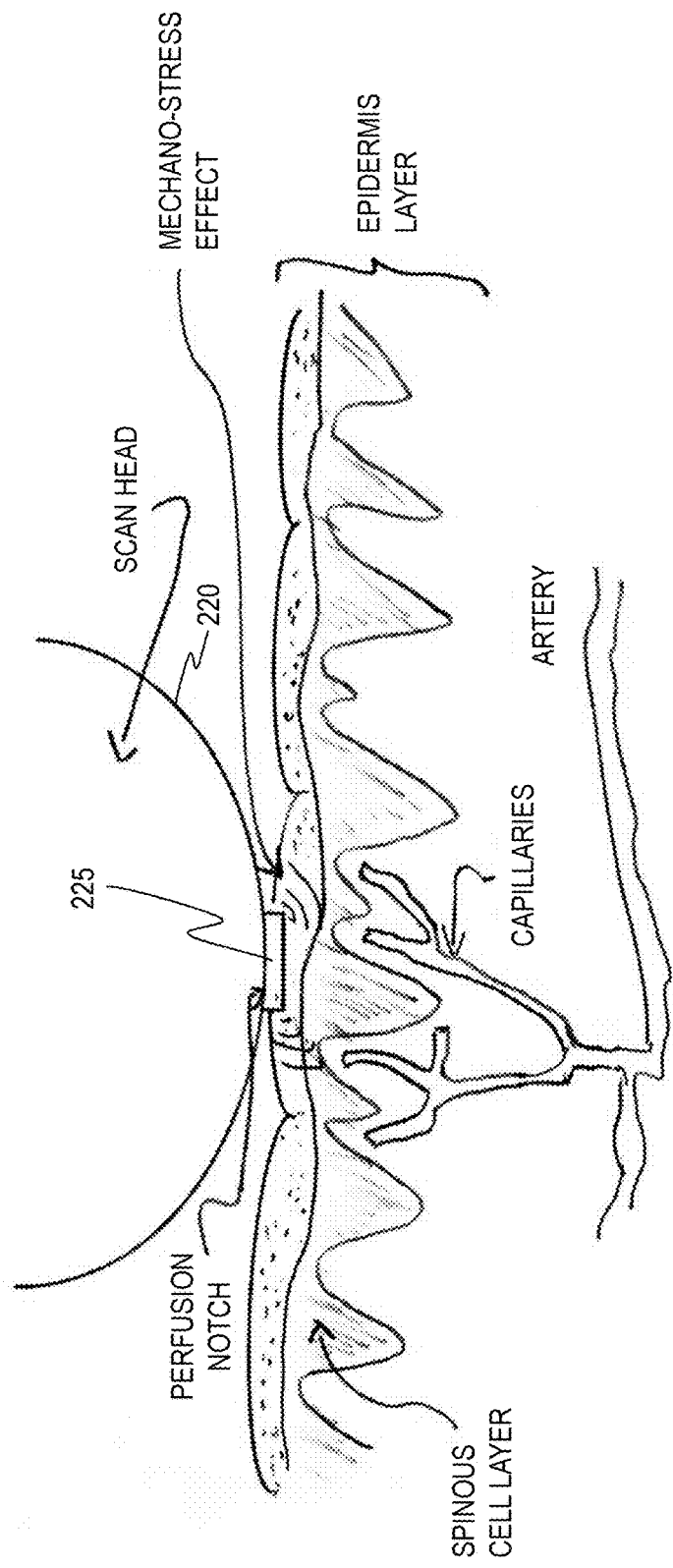

FIG. 1C2 is a schematic diagram 102 showing scan head 120 being used to assess tissue 98, according to some embodiments of the present invention. In some embodiments, incident LED light (from, e.g., light sources 122a and/or 122b) illuminates foot tissue 98 and is transmitted through tissue 98. In some embodiments, a percent of the incident light is absorbed in tissue 98, and an additional percent of the incident light is also specularly and diffusely reflected out of foot tissue 98 as shown in FIG. 1C2. In some embodiments, light sources 122a and 122b transmit near-IR light (e.g., in some embodiments, light source 122a emits light at a wavelength of approximately 760 nanometers (nm) and light source 122b emits light at a wavelength of approximately 850 nm) into the patient's foot tissue 98 and photodetector 123 receives the light after exposure with tissue 98. For example, in some embodiments, using a 940-nm light source provides the ability to detect wound exudate. Additional light sources at various wavelengths can also be incorporated into the design to increase optical resolution and detection capability. In some embodiments, a reflector panel 126 is incorporated in scan head 120 (see FIG. 1C1) to optimize reception of specular and diffused light.

The average path of the emitted NIR-light has been described as "banana-shaped" (see, e.g., FIG. 1C2 and van der Zee P., Arridge S., Cope M., Delpy D. (1990) "The effect of optode positioning on optical pathlength in near infrared spectroscopy of brain." Adv. Exp. Med. Biol. 277: 79-84). In some embodiments, specular light contains information on the vascular epidermis while diffuse light contains information about dermal vascularity and tissue perfusion diagnostics phenomena. In some embodiments, reflector panel 126 is designed to selectively control the amount of specular and diffuse light reflected to the photodetector 123.

FIG. 1D is a front-view schematic diagram of transducer 101, according to some embodiments of the present invention. The front-view of the transducer 101 with attached scan head 120, flexible neck 121, extension neck 110, articulated joint 107, and housing 105 with mechanical dimensions is highlighted in units of inches. (In FIG. 1D, the numbers at the left refer to the number of inches for this particular embodiment, and the commas represent the decimal place (as is the custom in Europe), wherein the metric centimeter equivalents for each such value can be obtained by multiplication by 2.54.) The overall height of the transducer 101 in some embodiments such as that shown in FIG. 1D is 16.73 inches (42.5 cm) with a width at base of the housing 105 as 1.5 inches (3.8 cm).

FIG. 1E is a top-view schematic diagram of transducer 101, according to some embodiments of the present invention. The mechanical dimensions of the base of housing 105 in this embodiment are 1.5 inches square (3.8 cm by 3.8 cm).

FIG. 1F is a side-view schematic diagram of transducer 101, according to some embodiments of the present invention, with attached scan head 120, flexible neck 121, extension neck 110, and housing 105. The length of the housing 105 in this embodiment is 6.38 inches (16.2 cm) plus about 0.75 inches (1.9 cm) to the centerline of the articulated joint 107 (thus housing 105 has a total length of about 7.9 inches (about 20 cm) in this embodiment), with a tapered base and an overall width of 1.5 inches (3.8 cm). In some embodiments, the flexible resilient neck 121 can flex up to 10 degrees by pressing against and/or pivoting the scan head.

FIG. 1G is a front-view schematic diagram of scan head 120, according to some embodiments of the present invention. FIG. 1G highlights certain details of the scan head 120, with the near-infrared LEDs 1221 and 122b (see FIG. 1C1) each located radially 0.08 inches (0.2 cm) from the center of scan head 120 in this embodiment, the photodetector 123 located radially 0.08 inches (0.2 cm) from the center of scan head 120 (again, see FIG. 1C1), and the optical window 124 has a radius of 0.5 inches.

FIG. 1H is a block diagram of a process 108 for assessing ulceration risk in a tissue, according to some embodiments of the present invention. In some embodiments, a patient 99 uses a handheld transducer 101 (see, e.g., FIG. 1A) to monitor foot tissue. In some embodiments, transducer 101 includes light emitter(s), a light sensor, accelerometers, a vibration mechanism, a pressure sensor, and a textured optical window. In some embodiments, RPI data is generated by transducer 101 and this RPI data is transmitted (e.g., wirelessly) to a smartphone/tablet (or other personal electronic device) 181. In some embodiments, smartphone 181 includes a software application (also referred to herein as an "app") that receives/stores/processes the transmitted RPI data and then sends a copy of the received/stored/processed RPI data to a central data aggregation and presentation system 182. In some embodiments, system 182 can be accessed by the patient's doctor or other medical professional 90 such that doctor 90 can follow patient 99's progress with process 108.

FIG. 2 is a schematic diagram 201 of a mechano-transduction-enhanced transducer 201 that creates a mechano-stress effect (e.g., an occlusion or ischemic condition) for a tissue. In some embodiments, scan head 220 of transducer 201 includes a perfusion notch 225 that provides a mechano-stress effect to the epidermis layer of a tissue by vibrating the tissue.

Figure 3:
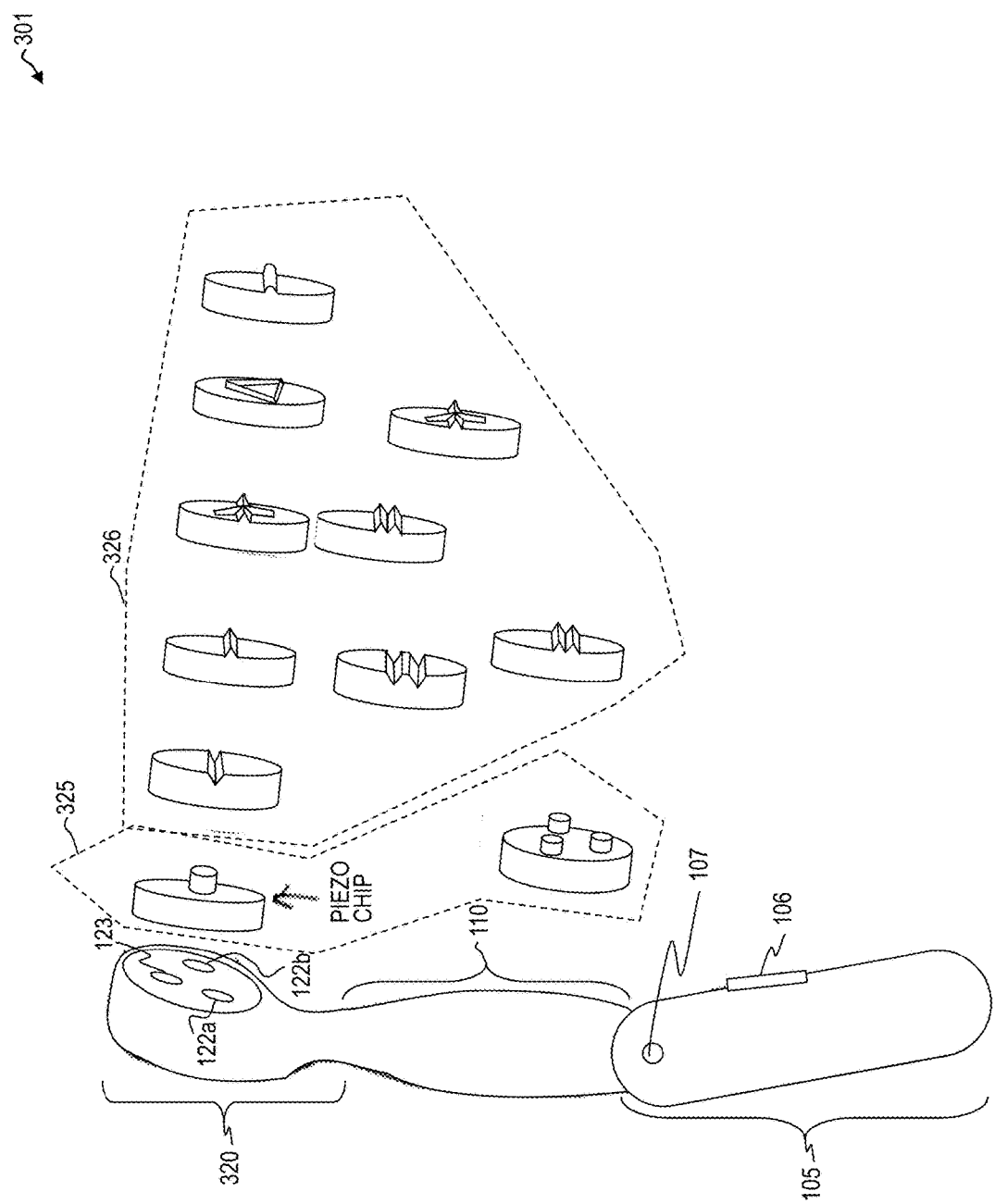
FIG. 3 is a schematic diagram of a transducer 301, according to some embodiments of the present invention.

FIG. 3 is a schematic diagram of a transducer 301, according to some embodiments of the present invention. In some embodiments, transducer 301 includes a housing 105, an articulated joint 107, an extension neck 110, a scan head 320, and, in some embodiments, transducer 301 is substantially similar to transducer 101 except that scan head 320 of transducer 301 is part of a kit that further includes a plurality of interchangeable vibration perception transducers 325 that can be affixed (e.g., in some embodiments, removably affixed) to scan head 320. In some embodiments, scan head 320 includes a threaded, grooved, or other feature that facilitates removably attaching one or more transducers 325 and/or optical windows 326. In some embodiments, each transducer 325 is configured to provide mechano-transduction (e.g., vibration) to the tissue during analysis of the tissue by transducer 301. In some embodiments, each transducer 325 includes an optical window that is transparent to the wavelengths of light used for the assessment performed by transducer 301. In some embodiments, each transducer 325 includes a piezoelectric vibration motor (e.g., a piezo chip). In some such embodiments, the vibration motor generates a modulation of the tissue-perfusion dynamics. In some embodiments, transducer 325 includes one or more raised areas (e.g., ridges or bumps) that protrude from the rest of the transducer 325 surface area. In some embodiments, transducer 325 includes one or more notches or dents that sink below the rest of the transducer 325 surface area. In some embodiments, transducer 301 is part of a kit that further includes a plurality of interchangeable textured-surface optical windows 326 that can be affixed (e.g., in some embodiments, removably affixed) to scan head 320. In some embodiments, each textured-surface optical windows 326 is configured to provide mechano-transduction (e.g., pressure and release of pressure by the patient pressing and sliding the textured transparent window across the skin of the foot) to the tissue during analysis of the tissue by transducer 301. In some embodiments, each optical window 326 includes a groove (e.g., in some embodiments, one or more grooves extending across a diameter), ridge (e.g., in some embodiments, one or more ridges extending across a diameter), bump(s), depression(s) or other suitable texture. In some embodiments, optical windows 326 include an opaque ring or circumference to keep stray light out.

In some embodiments, the output display of user interface panel 106 (see FIG. 1A) displays text and/or graphical instructions to the patient describing or showing the patient how to move the optical window of the scan head across the surface of the patient's foot or other tissue. In some embodiments, the output display of smartphone 181 (see FIG. 1H) displays text and/or graphical instructions to the patient describing to or showing the patient how to move the optical window of the scan head across the surface of the patient's foot or other tissue. In some embodiments, device 301 includes a plurality of accelerometers that detect the orientation of the scan head, and in some embodiments, data regarding the detected orientation is wirelessly transmitted to smartphone 181, wherein smartphone 181 analyzes the orientation data and provides displayed instructions to the patient based on the orientation information. In some embodiments, the device includes pressure and/or deflection transducers (e.g., in some embodiments, in a spring-loaded portion of flexible neck 121 of FIG. 1C1) that determine how much pressure is applied (e.g., the degree of tissue occlusion), and this pressure data is used in the analysis of the optical data and/or used to determine which instructions to display on display 106 of device 301 and/or on the display of smartphone 181. In some embodiments, the device 301 or smartphone 181 provides audio instructions (e.g., synthesized voice for the visually impaired).

Figure 4:
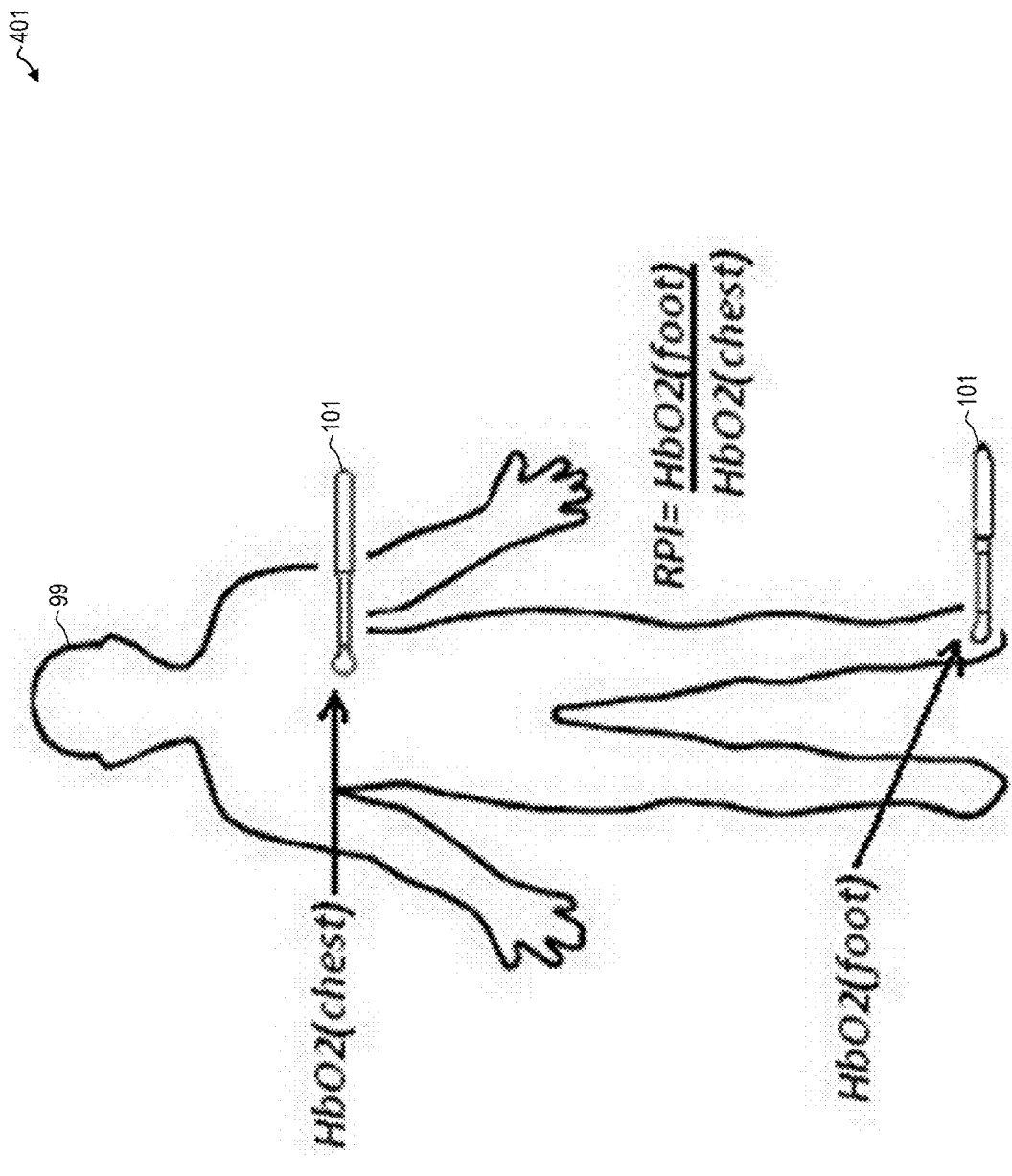
FIG. 4 is a schematic diagram showing a process 401 for assessing ulceration risk in a tissue of a patient 99.

FIG. 4 is a schematic diagram showing a process 401 for assessing ulceration risk in a tissue of a patient 99. In some embodiments, transducer 101 is first applied as a rolling scan device to the chest tissue of patient 99 and then transducer 101 is applied as a rolling scan device to the foot, in order to quantify $HbO_2$ levels of the chest and foot and estimate RPI (in some such embodiments, the RPI is equivalent to the $HbO_2$ value of the foot divided by the $HbO_2$ value of the chest).

Figure 5:
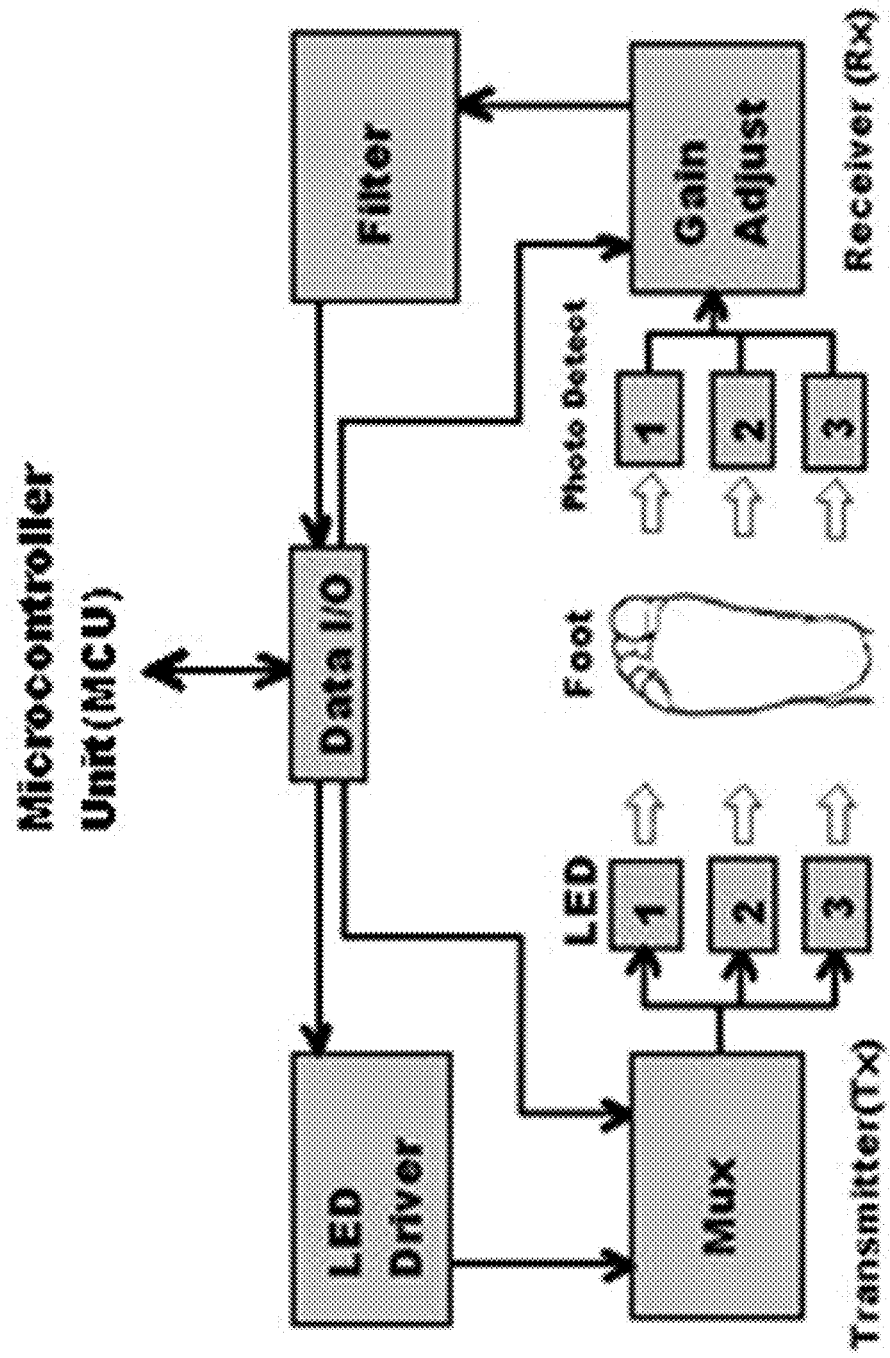
FIG. 5 is a block diagram of the operation 510 of a transducer optics assembly 501, according to some embodiments of the present invention.

FIG. 5 is a block diagram of the operation 510 of a transducer optics assembly 501, according to some embodiments of the present invention. In some embodiments, assembly 501 includes light sources 122a and 122b, and photodetector 123 (see FIG. 1C1) of transducer 101. In some embodiments, a time-multiplexed strobe signal is issued by the MCU to the LED driver circuit in the scan head electronics. In some embodiments, the transmitted LED light is detected by the receiver (i.e., photodetector) which converts the light to an equivalent voltage output. In some embodiments, the analog signal from the photodetector is measured by the MCU's analog-to-digital (A/D) converter, and digitized into 12 bits of resolution. In some embodiments, the transmitter section has an adjustable LED driver circuit and wavelength selector (e.g., in some embodiments, two or three wavelengths are used). In some embodiments, the LED driver adjusts and regulates the light output of the LED in order to compensate for absorption differences in various foot tissues. In some embodiments, for test subjects with lighter skin color, a lower level of LED intensity is adequate, while darker color skin requires higher intensity. The darker color skin causes a decrease in signal-to-noise ratio (SNR) by absorbing more light. In some embodiments, light intensity is adjusted by increasing or decreasing the current through the LED. In some embodiments a laser-diode light source is used to replace the LED light source to increase the optical power output to compensate for darker pigment skin-absorption effects. In some embodiments, one or more near-infrared (NIR) laser diodes is/are used (in place of, or in addition to, one or both of IR LEDs 122a and 122b) in order to increase the depth of near-infrared light penetration to examine sub-dermal tissue or connective bone tissue for ulceration risk. The depth of LED light penetration from IR LEDs 122a and 122b is typically limited to 2.0 to 3.0 mm into the tissue; however, the incorporation of one or more laser diodes increases the depth of penetration by a factor of two to four times. Another option for increasing optical power is to incorporate one or more vertical-cavity surface-emitting lasers (VCSELs) which emit a highly efficient optical beam vertically from their top surface(s). In some embodiments, such VCSELs use packaging similar to that of traditional low-cost LED packaging, thus reducing cost and improving integrability with existing photodiode detectors. In some embodiments, the range of current can be adjusted for 0 to 20 milliamps. In some embodiments, the transmitter also controls wavelength selection, defining which LED is activated, i.e., the 760 nm LED, or 850 nm LED (or corresponding laser diodes and/or VCSELs using such wavelengths). In some embodiments, the receiver section contains photodiodes to convert reflected and/or diffused light for each wavelength into an equivalent analog output signal. In some embodiments, an adjustable-gain amplifier increases the output signal level to optimize system dynamic range. In some embodiments, a low-pass filtering block with a cut-off frequency of one (1) Hz is implemented as an anti-alias filter to remove any aliasing and patient-motion frequency content prior to digitization. In other embodiments, a corresponding digital filter is implemented in a microprocessor to remove any aliasing and patient-motion frequency content after digitization.

Figure 6:
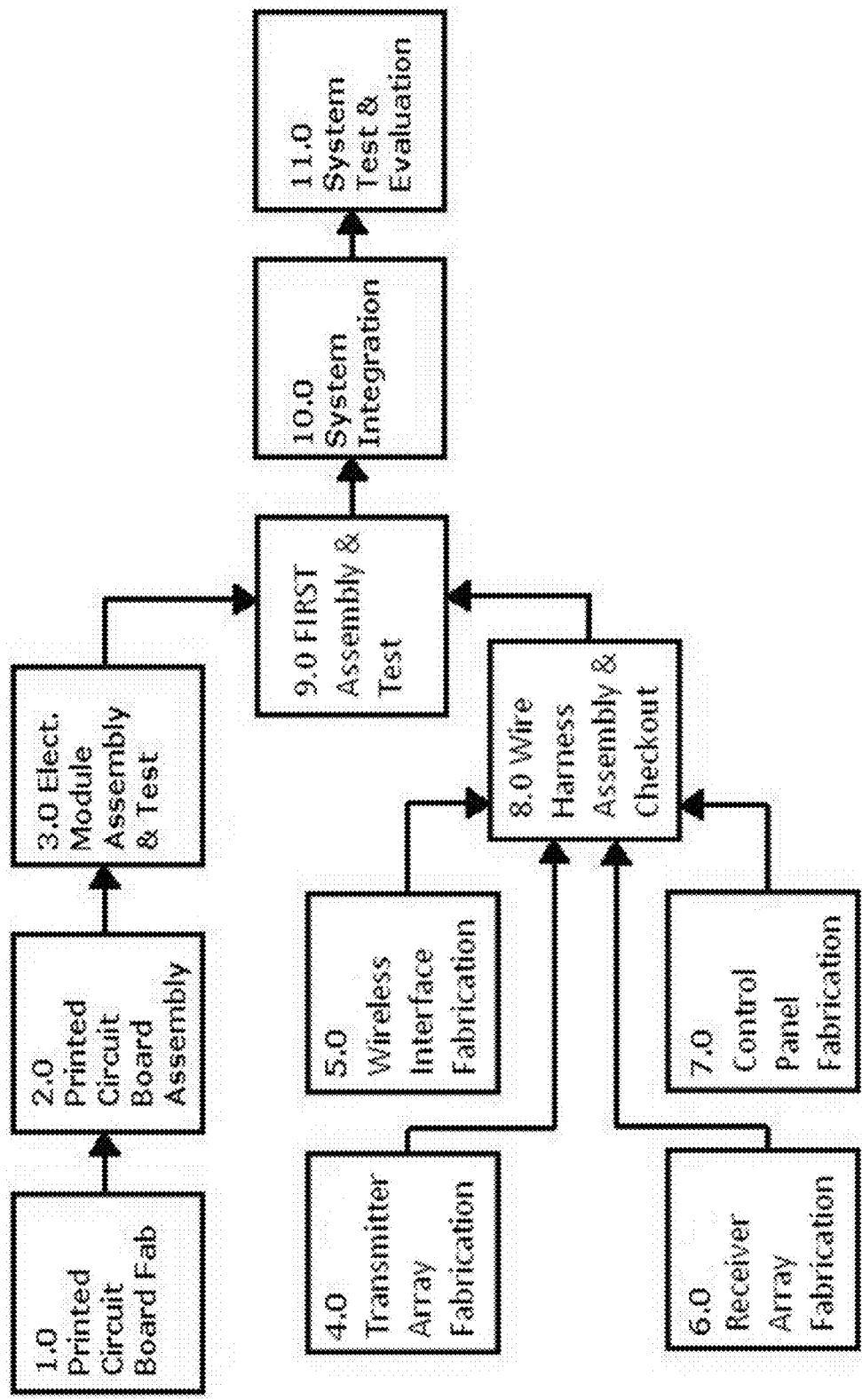
FIG. 6 is a block diagram of a product plan 601 for a diagnostic transducer, according to some embodiments of the present invention.

FIG. 6 is a block diagram of a product plan 601 for a diagnostic transducer, according to some embodiments of the present invention.

Figure 7A:
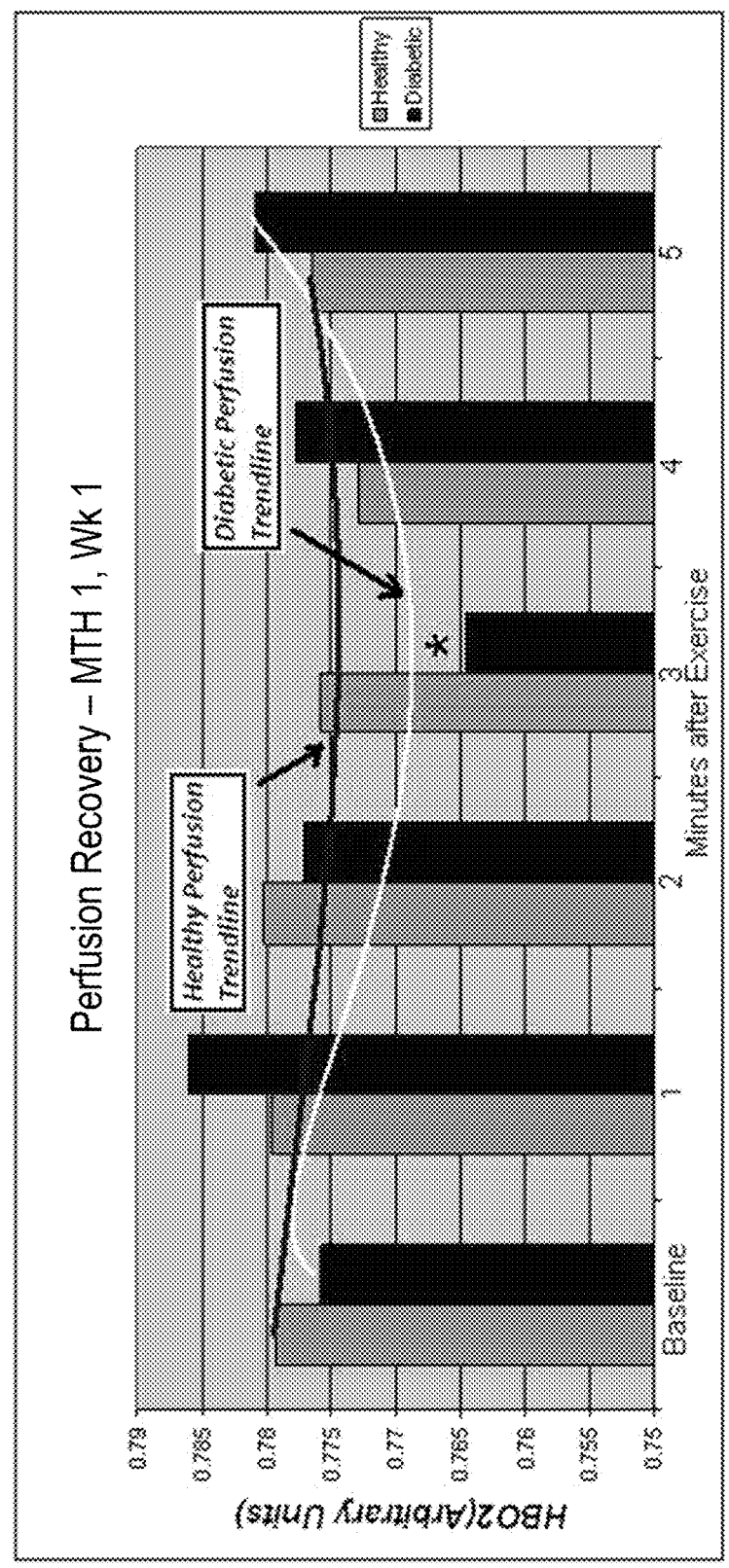
FIG. 7A is a graph 701 of perfusion recovery for the tissue on metatarsal head (MTH) number 1 at week 1.

FIG. 7A is a graph 701 of perfusion recovery for the tissue on metatarsal head (MTH) number 1 at week 1. Graph 701 includes MTH $HbO_2$ levels (as determined by a diagnostic transducer such as transducer 101 of FIG. 1A) for baseline and each minute of post-stress recovery (i.e., five minutes duration, one minute per scan). The diabetic data is compared with the healthy-subject data, averaging all $HbO_2$ levels together for five (5) diabetic subjects and six (6) healthy subjects for each week of the study. The lighter-shaded diagnostic trendline shows the pattern of perfusion recovery for the five diabetic subjects. The darker-shaded diagnostic trendline shows the pattern of perfusion recovery for the six healthy subjects. A baseline measurement was first performed (subject sitting in chair). A repetitive stress test was then performed, as a walking trial with their normal shoes at their chosen/natural gait for 10 minutes. After 10 minutes the subject was scanned for five minutes in post recovery, with one minute per transducer scan (10-second scan period). Each graph 7A, 7B, and 7C highlights the start of the recovery period with a "star marker" (minute 3 for week 1 and week 6, and minute 4 for week 12).

Figure 7B:
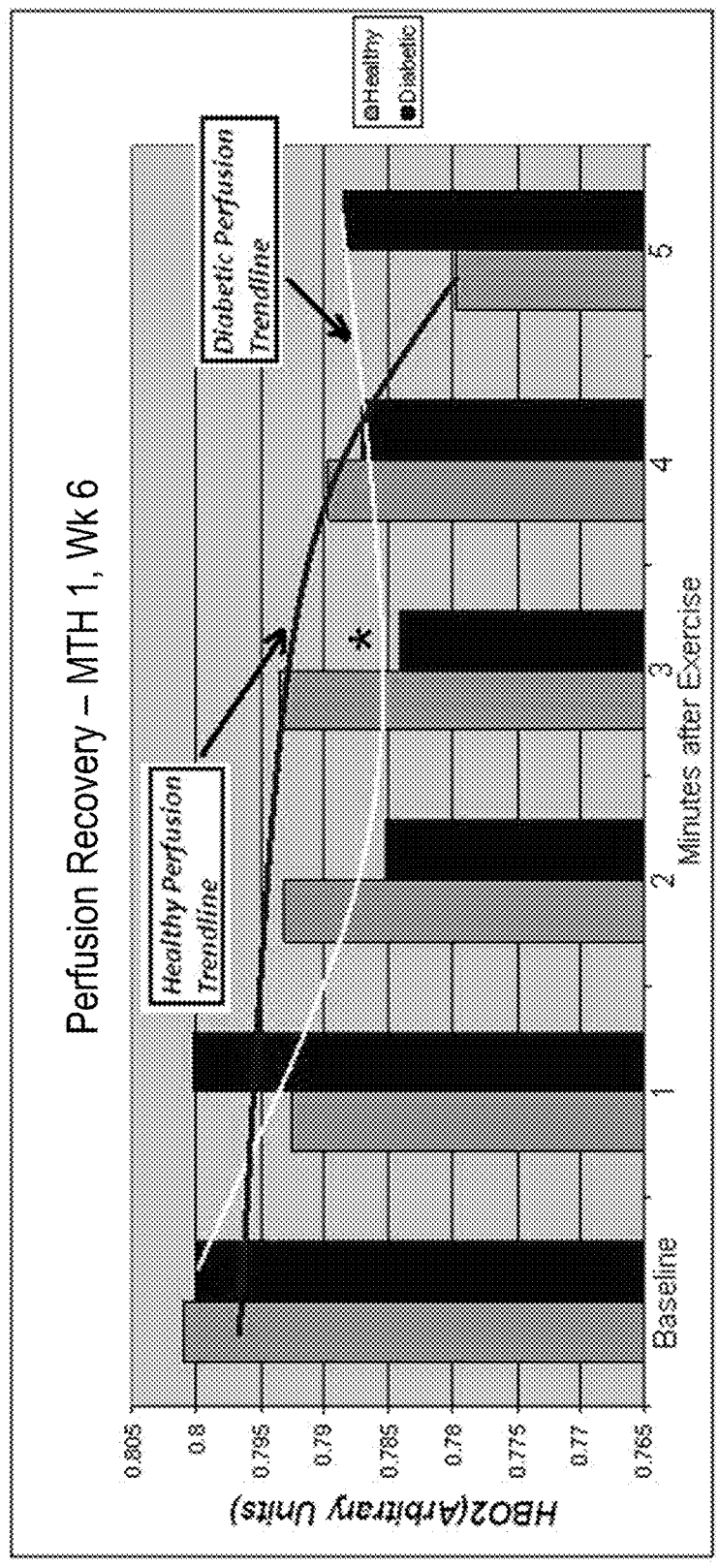
FIG. 7B is a graph 702 of perfusion recovery for the tissue on metatarsal head (MTH) number 1 at week 6.

FIG. 7B is a graph 702 of perfusion recovery for the tissue on metatarsal head (MTH) number 1 at week 6.

Figure 7C:
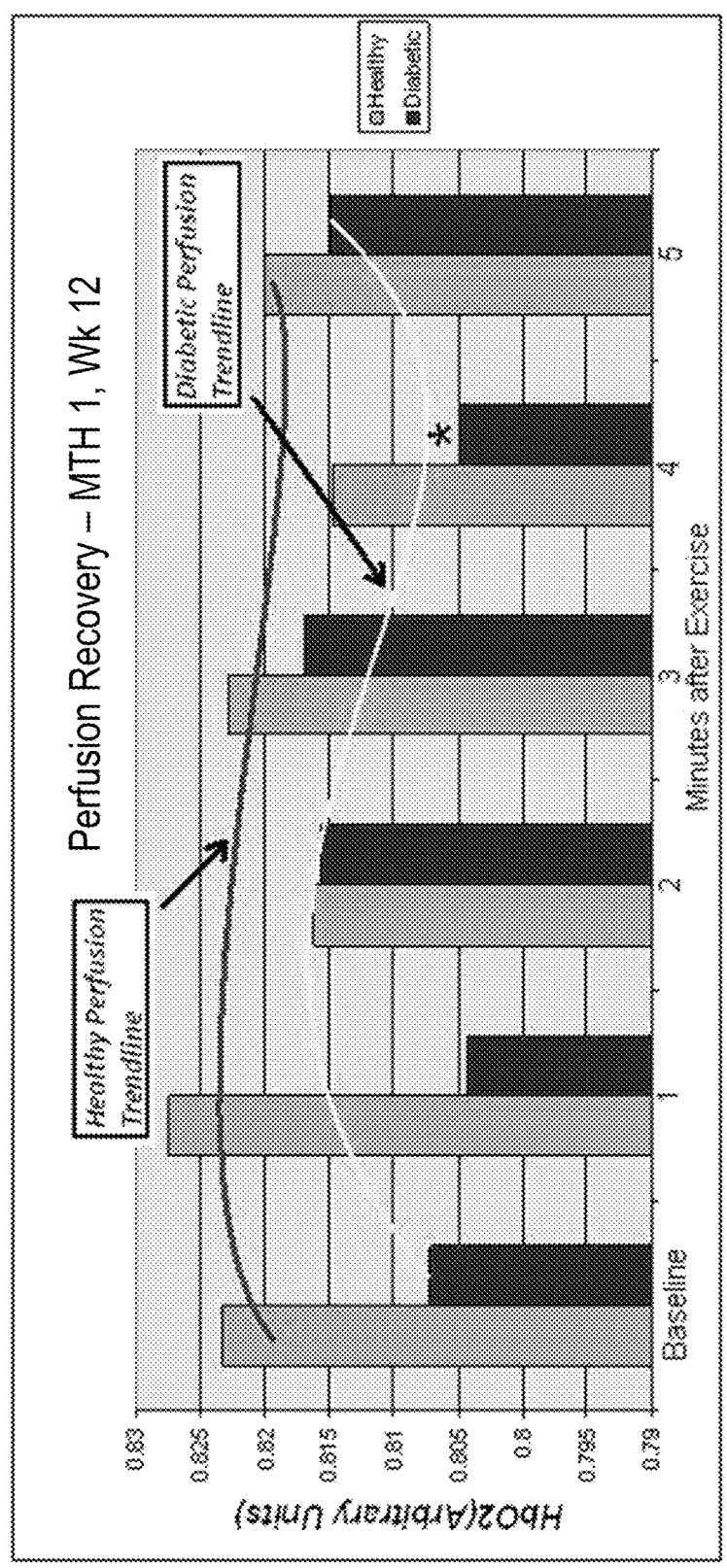
FIG. 7C is a graph 703 of perfusion recovery for the tissue on metatarsal head (MTH) number 1 at week 12.

FIG. 7C is a graph 703 of perfusion recovery for the tissue on metatarsal head (MTH) number 1 at week 12.

Figure 8A:
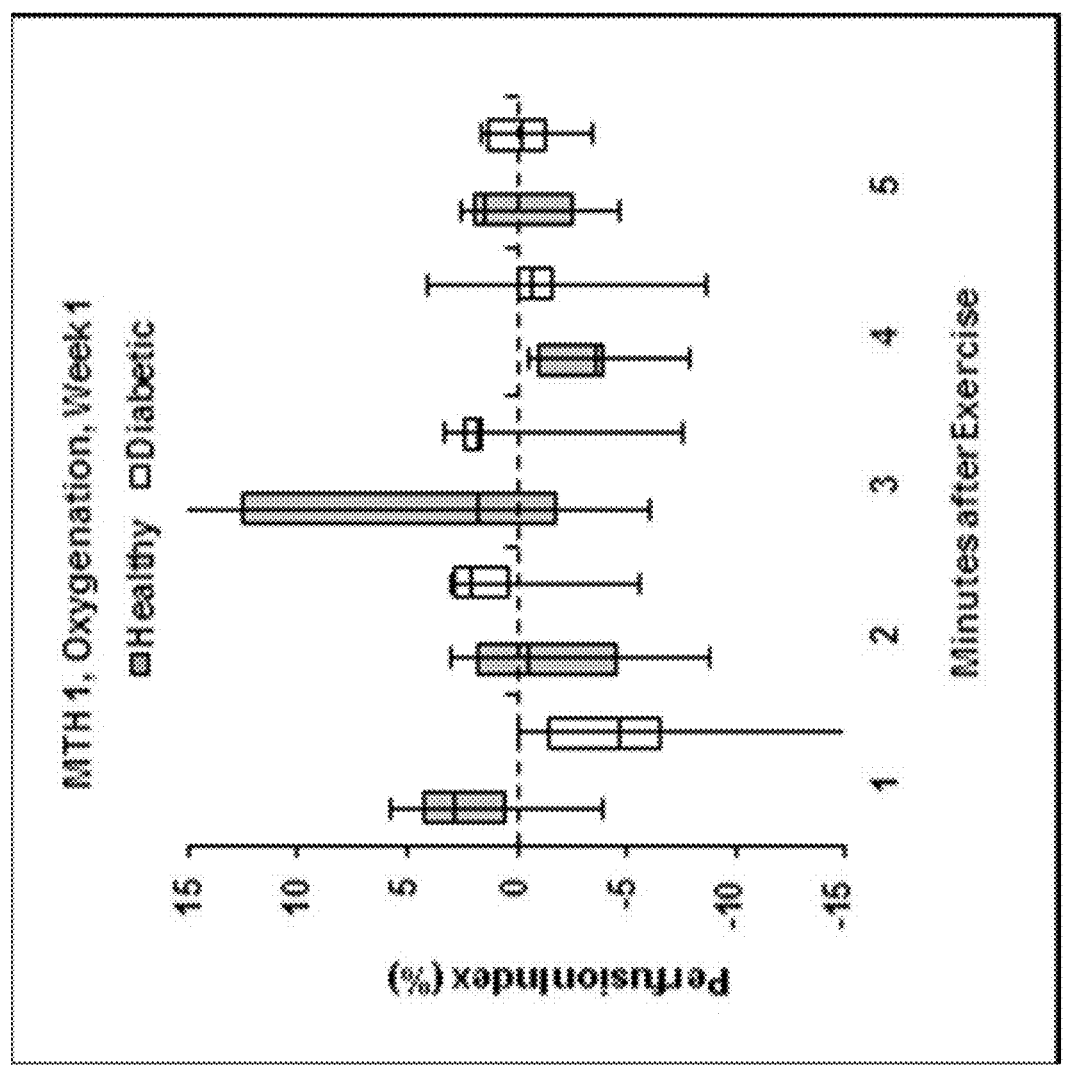
FIG. 8A is a graph 801 highlighting week 1 results comparing healthy subjects to diabetic subjects.

FIG. 8A is a graph 801 highlighting week 1 results comparing healthy subjects to diabetic subjects. The perfusion index is calculated by subtracting the oxygenation value from baseline value and dividing by the baseline. A comparison of weeks 6 and 12 indicates the increasing demand for oxygenation, i.e., reoxygenation in minutes 4 and 5 for the diabetic, which shows perfusion recovery in progress. This observation supports the perfusion recovery results shown in FIGS. 7A-7C.

Figure 8B:
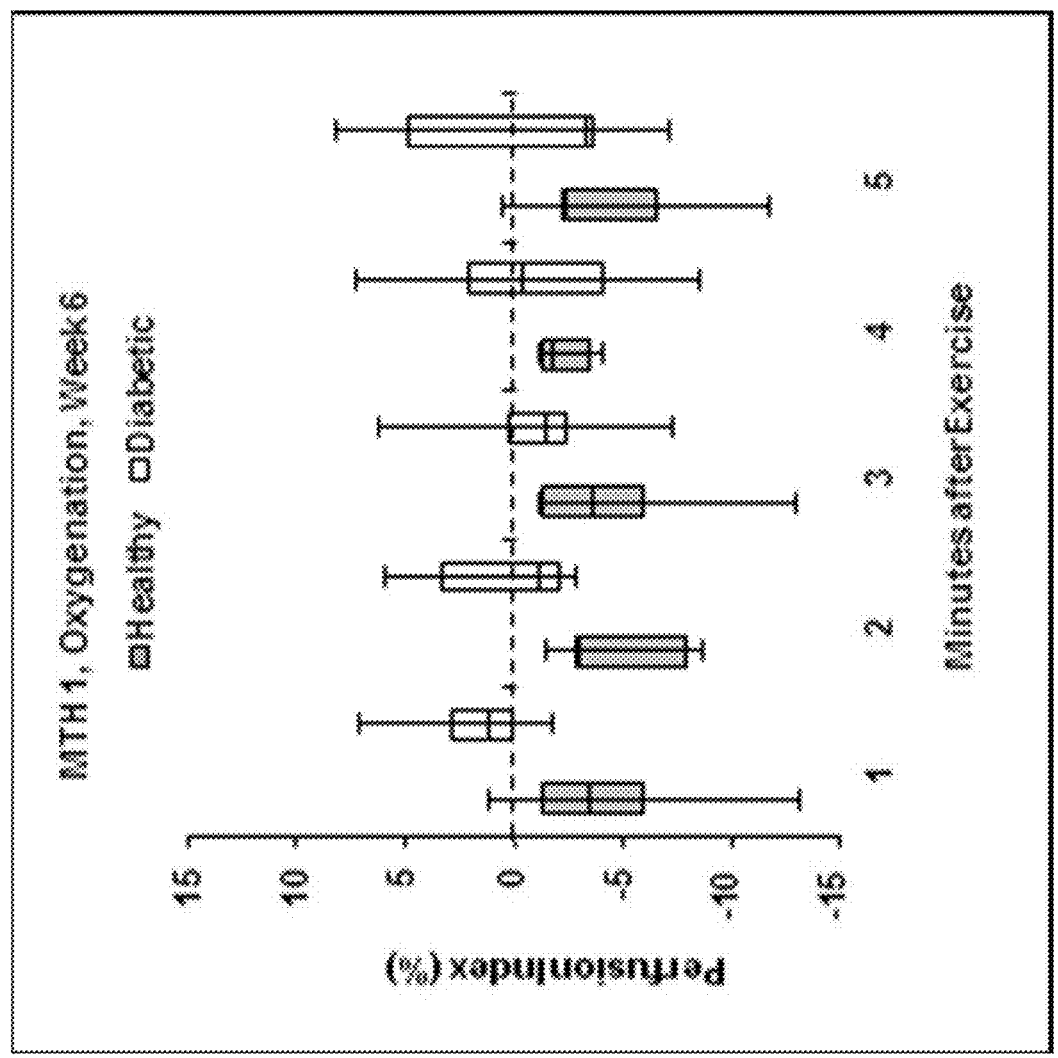
FIG. 8B is a graph 802 highlighting week 6 results comparing healthy subjects to diabetic subjects.

FIG. 8B is a graph 802 highlighting week 6 results comparing healthy subjects to diabetic subjects.

Figure 8C:
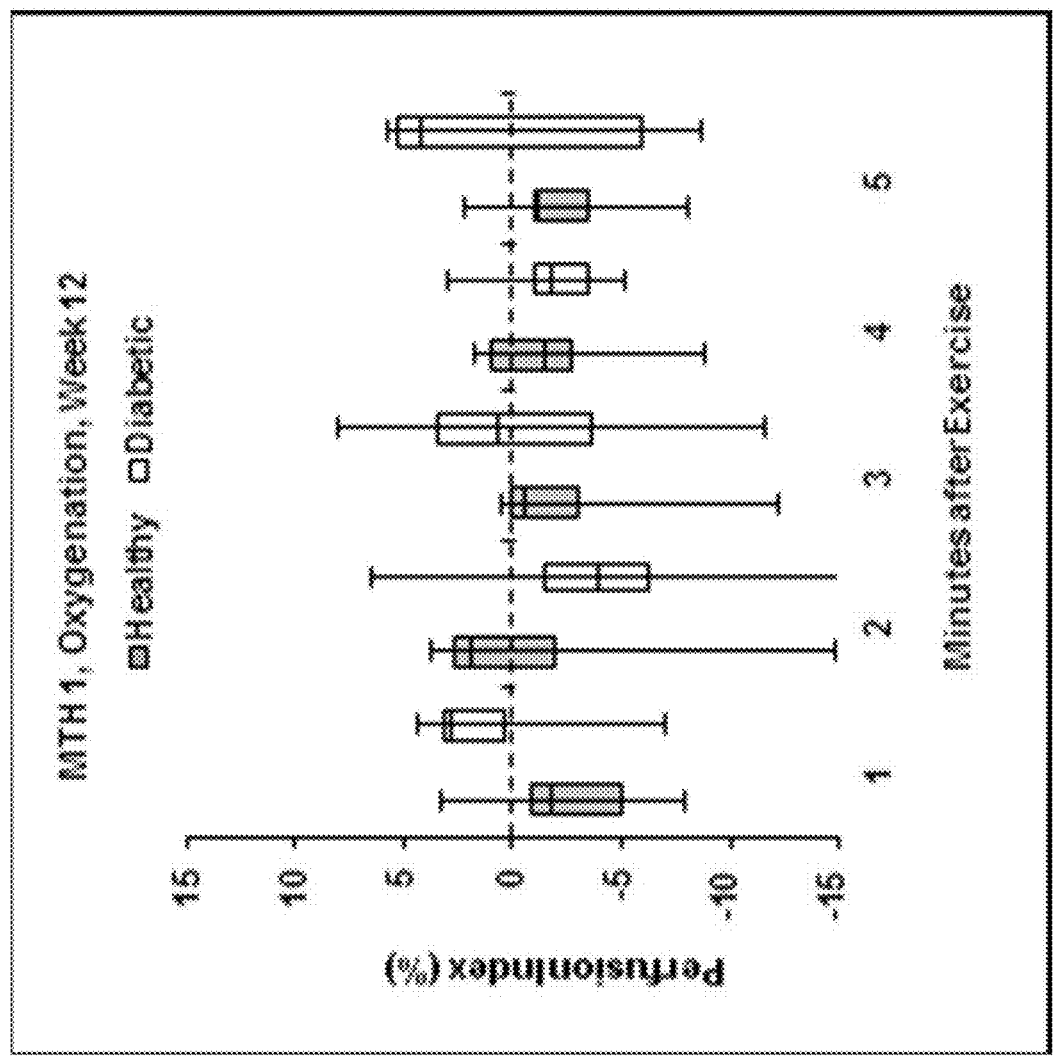
FIG. 8C is a graph 803 highlighting week 12 results comparing healthy subjects to diabetic subjects.

FIG. 8C is a graph 803 highlighting week 12 results comparing healthy subjects to diabetic subjects.

Figure 9A:
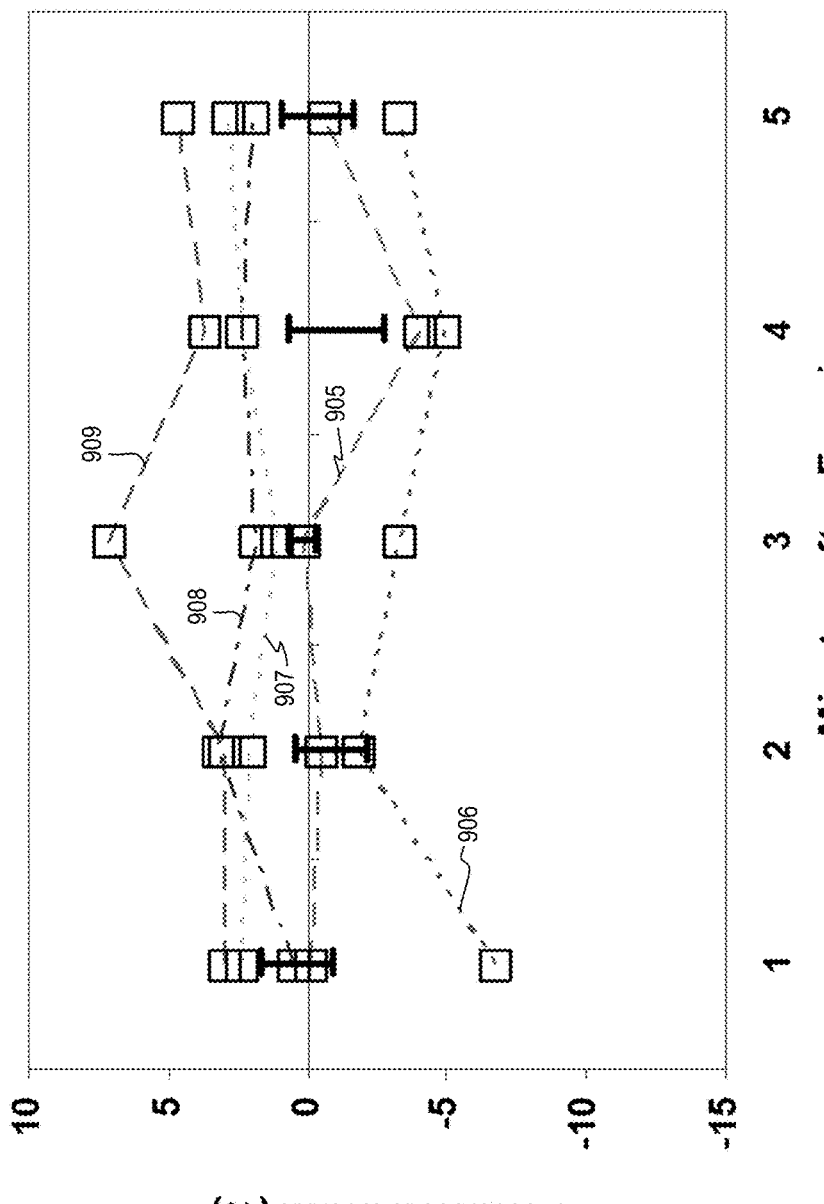
FIG. 9A is a graph 901 showing the perfusion recovery of individual diabetic subjects at week 1.

FIG. 9A is a graph 901 showing the perfusion recovery of individual diabetic subjects at week 1. The healthy-subject data is shown as the standard deviation. Data line 905 corresponds to a 71-year-old Caucasian male diagnosed with diabetes in 1996 (referred to as RLV on the graph legend), data line 906 corresponds to an 80-year-old Caucasian male diagnosed with diabetes in 1998 (referred to as TS on the graph legend), data line 907 corresponds to a 67-year-old Caucasian male diagnosed with diabetes in 1971 (referred to as APH on the graph legend), data line 908 corresponds to a 42-year-old Hispanic male diagnosed with diabetes in 2005 (referred to as PC on the graph legend), and data line 909 corresponds to a 52-year-old African-American male diagnosed with diabetes in 2000 (referred to as AW on the graph legend).

Figure 9B:
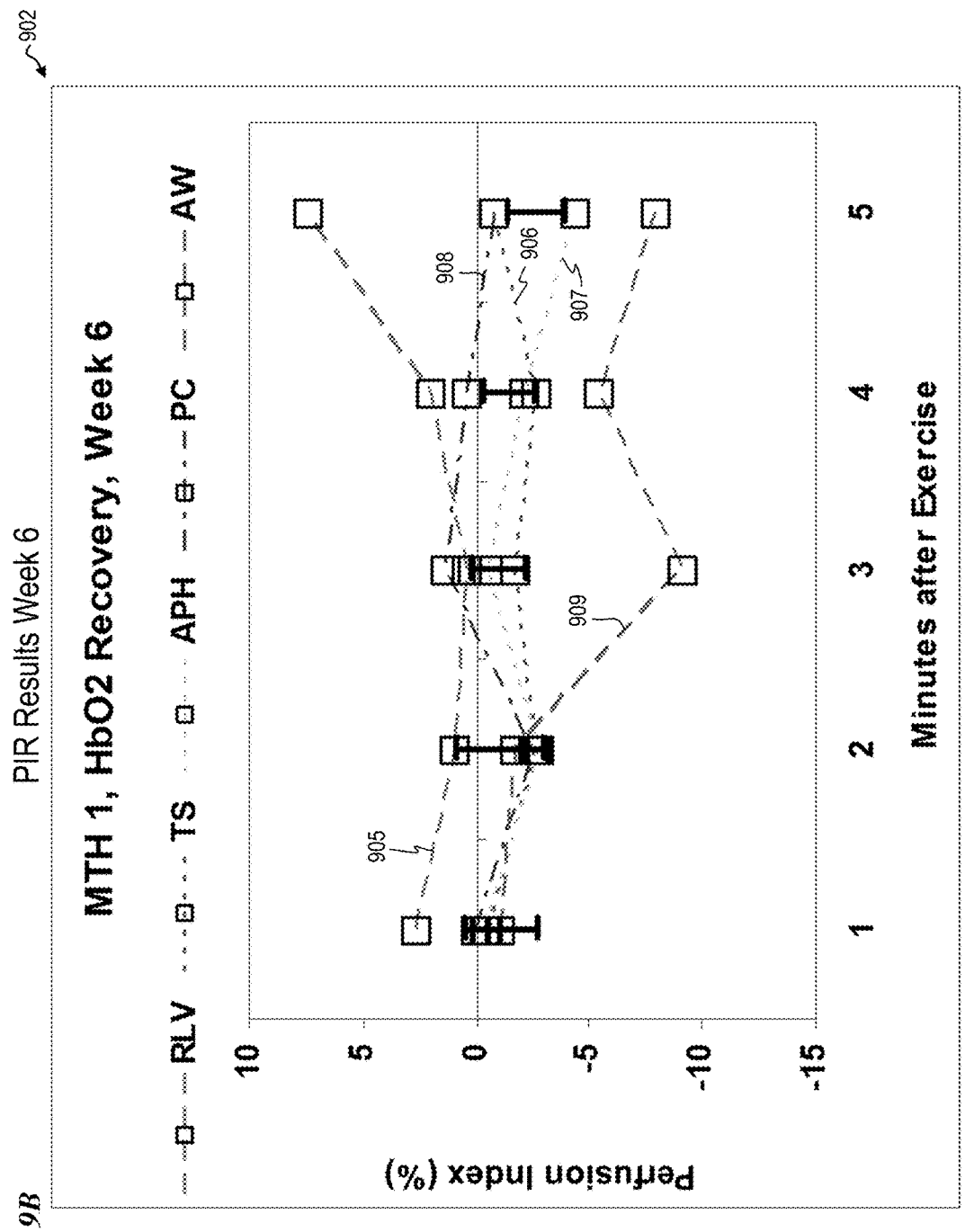
FIG. 9B is a graph 902 showing the perfusion recovery of individual diabetic subjects at week 6.

FIG. 9B is a graph 902 showing the perfusion recovery of individual diabetic subjects at week 6.

Figure 9C:
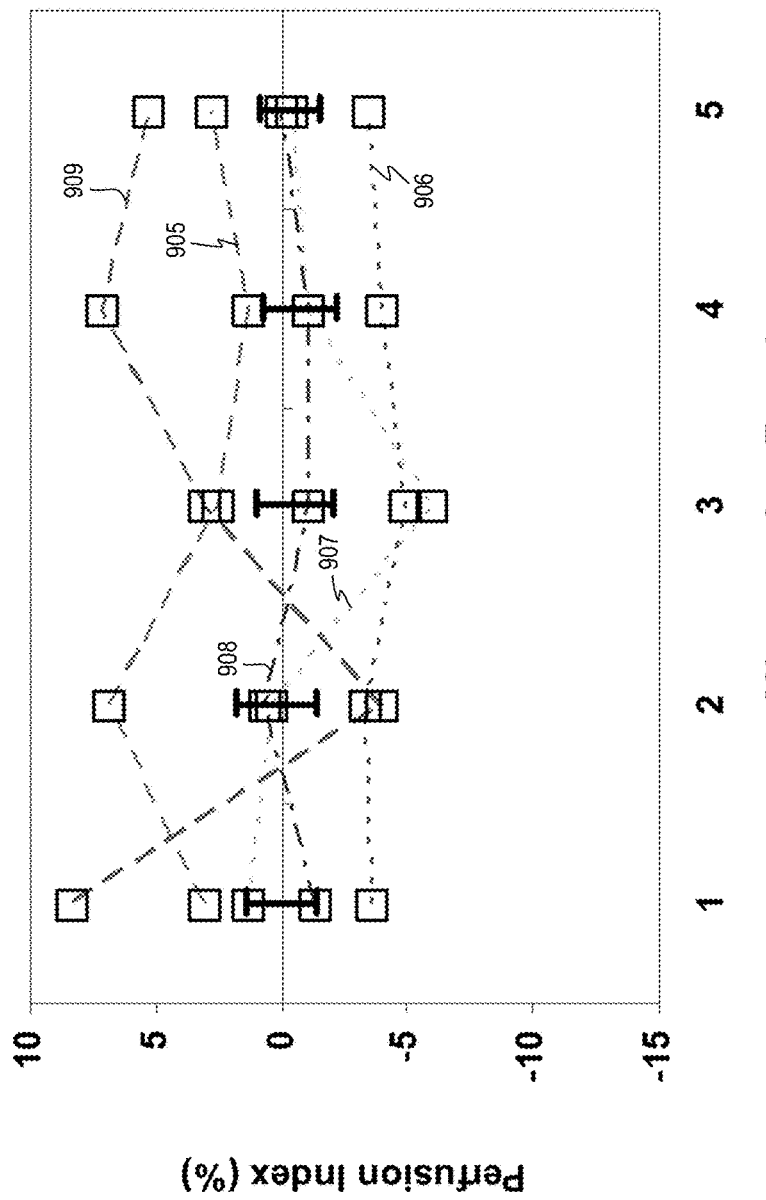
FIG. 9C is a graph 903 showing the perfusion recovery of individual diabetic subjects at week 12.

FIG. 9C is a graph 903 showing the perfusion recovery of individual diabetic subjects at week 12.

Figure 10A:
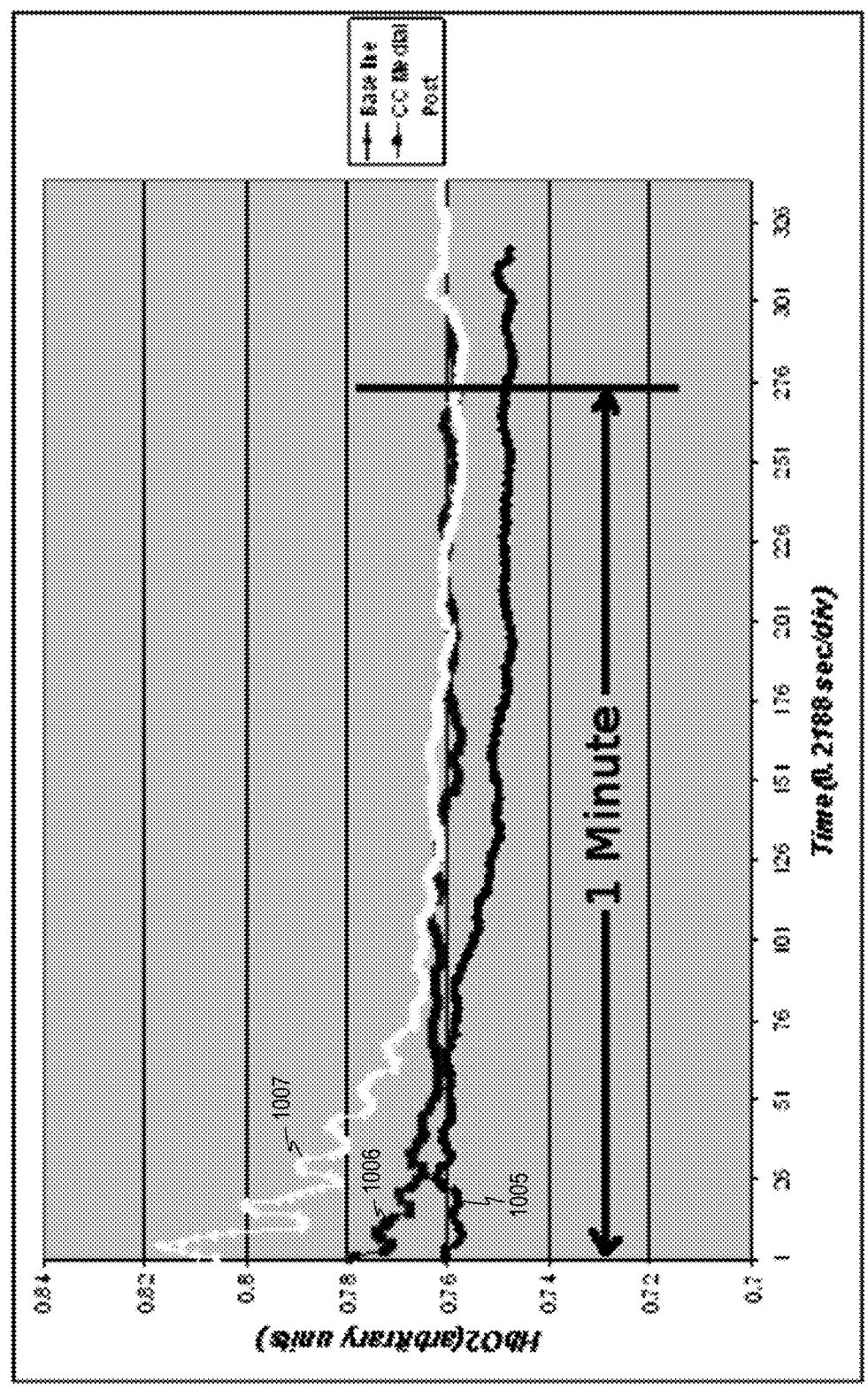
FIG. 10A is a graph 1001 showing oxygenated hemoglobin levels during mechano-transduction testing on a healthy control subject.

FIG. 10A is a graph 1001 showing oxygenated hemoglobin levels during mechano-transduction testing on a healthy control subject. The healthy subject was a 39-year-old Caucasian female. Data line 1005 corresponds to a baseline time period, data line 1006 corresponds to a mechano-transduction period, and data line 1007 corresponds to a one (1) minute post-recovery period. During the baseline period of data line 1005, the subject was sitting in a chair at rest for five (5) minutes with their feet on a chair and with a diagnostic transducer (according to one embodiment of the present invention) pressed against the medial side of metatarsal head (MTH) number (no.) 1. During the mechano-transduction period of data line 1006, a vibration perception transducer (VPT) (e.g., a meter such as the Sensitometer-VPT provided by Dhansai Laboratory, www.dhansai.com/sensitometerVpt.html, or the VPT Meter provided by Xilas Medical, www.alanweinkrantz.com/xilass_vpt_vibr/) was applied on the medial side of MTH No. 1 concurrently with the diagnostic transducer. During the post-recovery period of data line 1007, the subject was sitting in the chair at rest with the diagnostic transducer applied to the medial side of MTH No. 1.

Figure 10B:
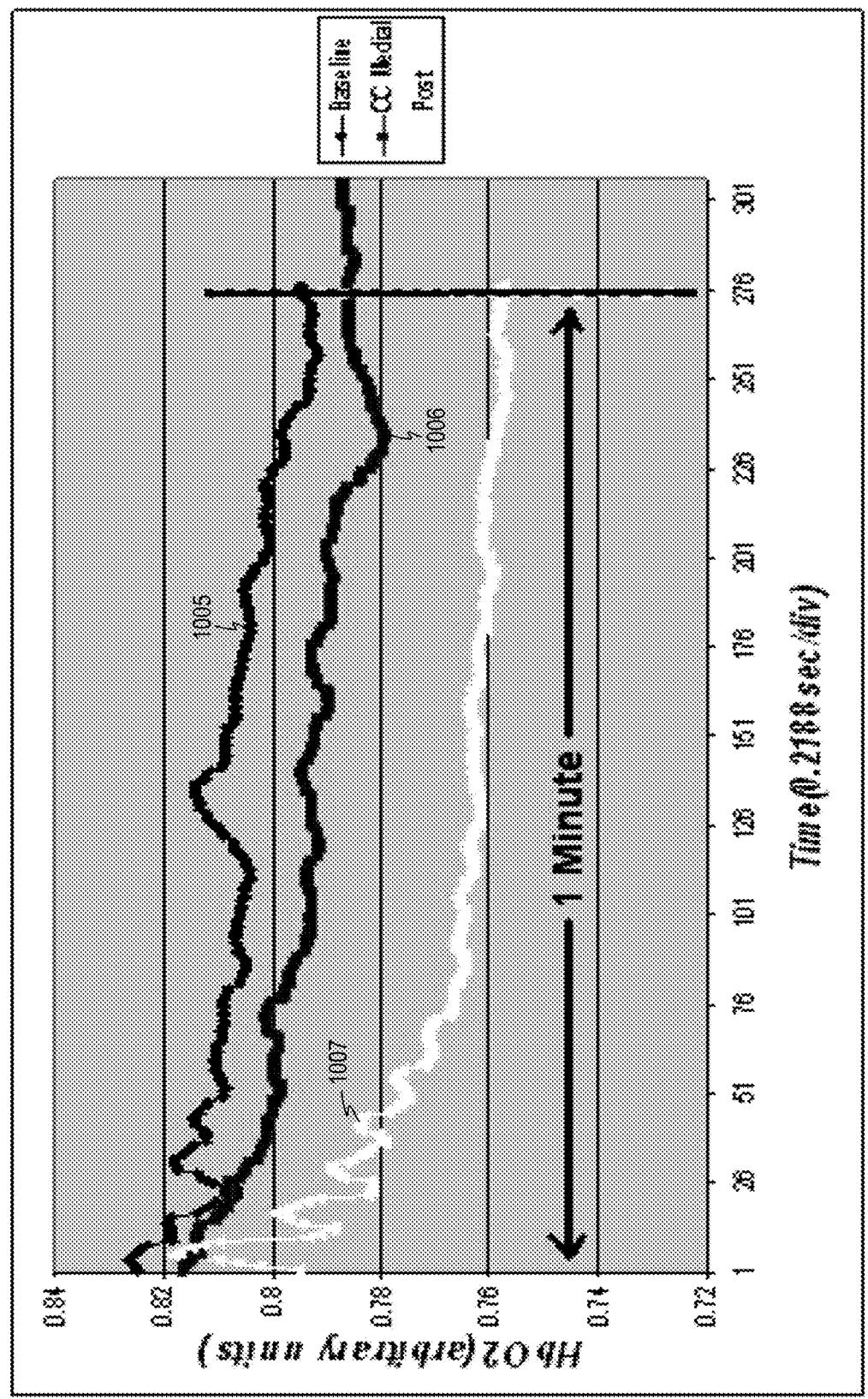
FIG. 10B is a graph 1002 showing oxygenated hemoglobin levels during mechano-transduction testing on a subject with diabetes mellitus and peripheral neuropathy (DMPN).

FIG. 10B is a graph 1002 showing oxygenated hemoglobin levels during mechano-transduction testing on a subject with diabetes mellitus and peripheral neuropathy (DMPN). The DMPN subject was a 42-year-old African-American male.

Figure 10C:
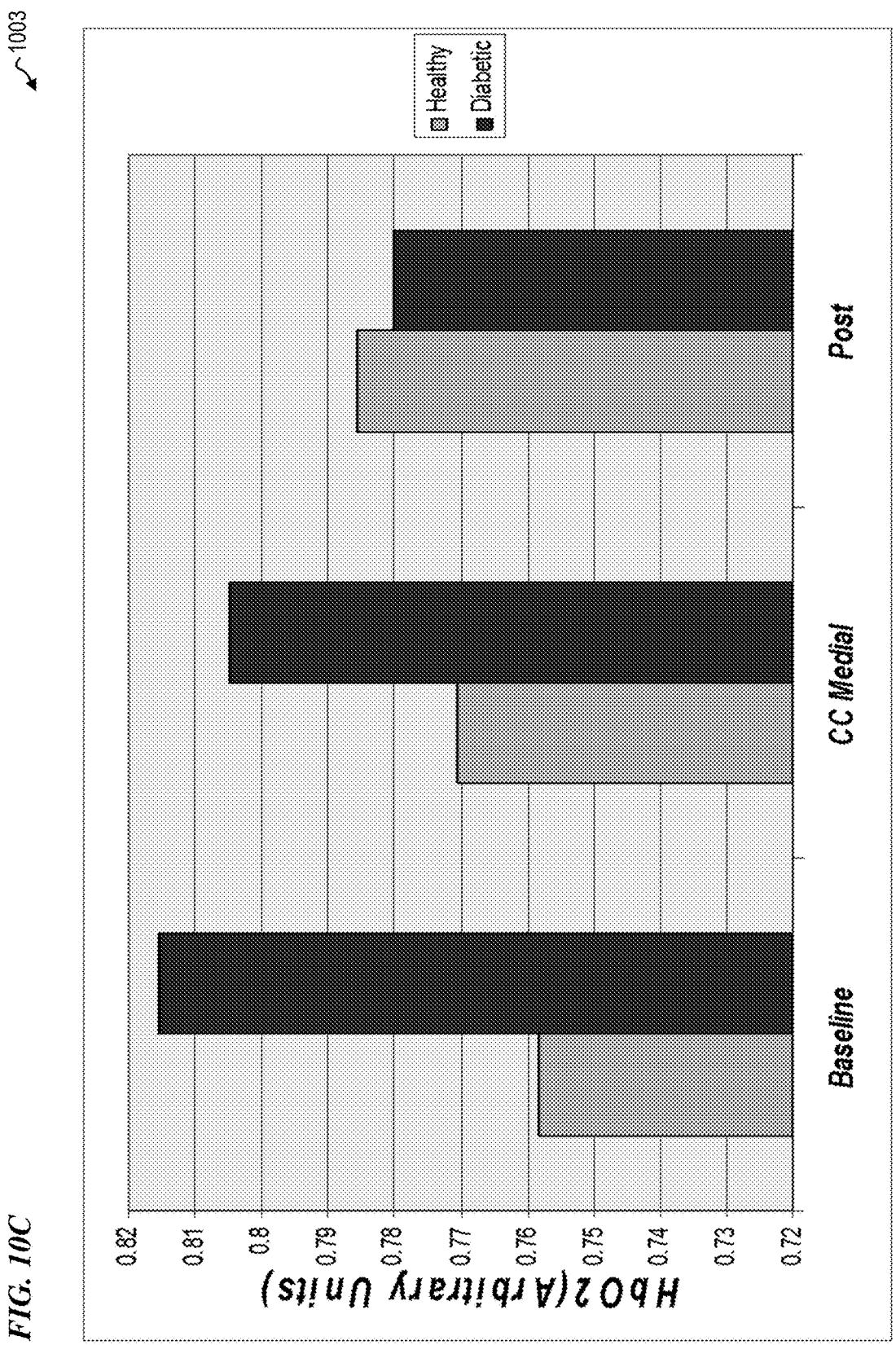
FIG. 10C is a graph 1003 showing the average oxygenated hemoglobin ($HbO_2$) levels of the healthy subject and the DMPN subject for the first 20 seconds of each activity period (baseline, mechano-transduction, and post-recovery).

FIG. 10C is a graph 1003 showing the average oxygenated hemoglobin ($HbO_2$) levels of the healthy subject and the DMPN subject for the first 20 seconds of each activity period (baseline, mechano-transduction, and post-recovery).

In some embodiments, the present invention provides a diagnostic device for assessing ulceration risk in a tissue, the device including a housing, wherein the housing includes a user interface; an extension neck operatively coupled to the housing at a first end of the extension neck, wherein the extension neck has at least a first range of motion relative to the housing; a scan head operatively coupled to the extension neck at a second end of the extension neck, wherein the scan head has at least a second range of motion relative to the extension neck, wherein the scan head includes: a light-emitting system configured to emit light at a selected wavelength of a predetermined set of wavelengths at a first time and to direct the emitted light into the tissue; and a photodetector configured to receive light reflected from the tissue (e.g., due to absorption of oxyhemoglobin) and generate an electrical signal based on the received reflected light; a controller operatively coupled to the user interface and configured to control the light-emitting system and the photodetector; and a processor operatively coupled to the photodetector and the controller and configured to calculate regional-perfusion-index (RPI) data based at least in part on the electrical signal generated by the photodetector.

In some embodiments of the device, the scan head includes an optical window, wherein the light-emitting system is configured to transmit the emitted light through the optical window and into the tissue, and wherein the photodetector is configured to receive the reflected light through the optical window. In some embodiments, the light-emitting system includes a first laser configured to emit a first infrared (IR) wavelength at the first time and a second laser configured to emit a second IR wavelength at a second time. In some embodiments, the light-emitting system includes a first light-emitting diode (LED) configured to emit a first infrared (IR) wavelength at the first time and a second LED configured to emit a second IR wavelength at a second time. In some embodiments, the light-emitting system includes a single laser operable to emit light at different ones of the predetermined set of wavelengths at different times, wherein the predetermined set of wavelengths include a first wavelength of approximately 760 nanometers (nm) and a second wavelength of approximately 850 nm. In some embodiments, the diagnostic device is configured to be handheld and battery powered.

In some embodiments of the device, the scan head includes a removable mechano-transduction module configured to provide repetitive mechanical stress to the tissue. In some embodiments, the scan head includes a removable mechano-transduction module configured to provide repetitive mechanical stress to the tissue, and wherein the mechano-transduction module includes a piezoelectric vibration motor. In some embodiments, the scan head includes an optical window, wherein the light-emitting system is configured to transmit the emitted light through the optical window and into the tissue, wherein the photodetector is configured to receive the reflected light through the optical window, wherein the optical window includes at least a first raised surface area, and wherein the optical window is configured to provide repetitive mechanical stress to the tissue.

In some embodiments of the device, the scan head includes an optical window, wherein the light-emitting system is configured to transmit the selected wavelength through the optical window and into the tissue, wherein the photodetector is configured to receive the reflected light through the optical window, wherein the optical window includes at least a first raised surface area and a piezoelectric vibration motor, and wherein the optical window is configured to provide repetitive mechanical stress to the tissue via the at least first raised surface area and the piezoelectric vibration motor.

In some embodiments of the device, the scan head includes a reflector panel configured to selectively control an amount of specular and diffuse light reflected to the photodetector. In some embodiments, the scan head is made from a material that includes medical-grade acrylonitrile butadiene styrene (ABS). In some embodiments, the user interface includes an organic light-emitting diode (OLED) configured to provide adjustable optical power and to display remaining battery life and the RPI data.

In some embodiments of the device, the scan head further includes an optical window that is textured on its skin-facing surface, and wherein the processor is configured to determine the RPI data as the patient presses the optical window against the tissue and moves the scan head across the tissue to provide pressure differences to different portions of the tissue over time.

In some embodiments of the device, the scan head further includes an optical window that includes a transverse groove on an outer surface, and wherein the processor is configured to determine the RPI data as the patient presses the optical window against the tissue and moves the scan head across the tissue to provide pressure differences to different portions of the tissue over time.

In some embodiments of the device, the scan head further includes an optical window that includes a transverse ridge on an outer surface, and wherein the processor is configured to determine the RPI data as the patient presses the optical window against the tissue and moves the scan head across the tissue to provide pressure differences to different portions of the tissue over time.

In some embodiments of the device, the diagnostic device is configured to be handheld and battery powered. In some embodiments of the device, the scan head includes a mechano-transduction vibration module configured to provide repetitive mechanical stress to the tissue.

In some embodiments of the device, the scan head includes an optical window, wherein the light-emitting system is configured to transmit the emitted light through the optical window and into the tissue, wherein the photodetector is configured to receive the reflected light through the optical window, wherein the optical window includes at least a first raised surface area, and wherein the optical window is configured to provide repetitive mechanical stress to the tissue.

In some embodiments of the device, the scan head includes a reflector panel configured to selectively control an amount of specular and diffuse light reflected to the photodetector.

In some embodiments of the device, the scan head is made from a material that includes medical-grade acrylonitrile butadiene styrene (ABS).

In some embodiments of the device, the user interface includes an organic light-emitting diode (OLED) configured to provide adjustable optical power and to display remaining battery life and the RPI data.

In some embodiments, the present invention includes a kit that includes the handheld scan device, and a plurality of replaceable optical windows (e.g., in some embodiments, a set such as collection 325 of FIG. 3) that have different surface topologies, such that different diagnoses can be achieved by changing to one of the plurality of replaceable optical windows that are specifically suited to the different diagnoses.

In some embodiments, the present invention provides a method for assessing ulceration risk in a tissue, the method including providing a diagnostic device that includes a scan head and a user interface, wherein the scan head includes a light-emitting system and a photodetector; rolling the scan head in a medial and lateral direction across the tissue; emitting light at a selected wavelength of a predetermined set of wavelengths from the light-emitting system at a first time and directing the emitted light into the tissue; receiving light reflected from the tissue at the photodetector and generating an electrical signal based on the received reflected light; calculating regional-perfusion-index (RPI) data based at least in part on the electrical signal; and displaying the RPI data via the user interface.

In some embodiments of the method, the scan head further includes an optical window, and wherein the emitting includes transmitting the emitted light through the optical window and into the tissue. In some embodiments, the light-emitting system includes a first laser and a second laser, wherein the emitting includes emitting light at a first infrared (IR) wavelength from the first laser at the first time and emitting light at a second IR wavelength from the second laser at a second time. In some embodiments, the light-emitting system includes a first light-emitting diode (LED) and a second LED, wherein the emitting includes emitting light at a first infrared (IR) wavelength from the first LED at the first time and emitting light at a second IR wavelength from the second LED at a second time.

In some embodiments of the method, the displaying includes indicating a concentration of deoxygenated hemoglobin (deoxy-Hb) and oxygenated hemoglobin (oxy-Hb) in blood flowing through the tissue. In some embodiments, the light-emitting system includes a single laser diode operable to emit light at different ones of the predetermined set of wavelengths at different times, wherein the predetermined set of wavelengths include a first wavelength of approximately 760 nanometers (nm) and a second wavelength of approximately 850 nm.

In some embodiments, the method further includes providing a repetitive mechanical stress to the tissue. In some embodiments, the method further includes transmitting the RPI data to a storage medium. In some embodiments, the method further includes transmitting the RPI data wirelessly to a personal electronic device. In some embodiments of the method, the rolling includes rolling the scan head in a medial and lateral direction across chest tissue and rolling the scan head in a medial and lateral direction across foot tissue, wherein the RPI data includes an RPI value that is equivalent to a first oxygenated hemoglobin value of the chest tissue divided by a second oxygenated hemoglobin value of the foot tissue.

In some embodiments, the present invention provides a diagnostic device for assessing ulceration risk in a tissue, the device including a housing, wherein the housing includes a user interface panel; an extension neck operatively coupled to the housing at a first end of the extension neck, wherein the extension neck has at least a first range of motion relative to the housing; a scan head operatively coupled to the extension neck at a second end of the extension neck, wherein the scan head has at least a second range of motion relative to the extension neck, wherein the scan head includes: a first light source configured to transmit light at a first wavelength into the tissue; and a photodetector configured to receive light reflected from the tissue and generate an electrical signal based on the received reflected light; a controller operatively coupled to the user interface and configured to control the first light source and the photodetector; and a processor operatively coupled to the photodetector and the controller and configured to determine a regional-perfusion-index (RPI) value based at least in part on the electrical signal generated by the photodetector.

In some embodiments of the device, the scan head further includes an optical window, wherein the first light source is configured to transmit the light at the first wavelength through the optical window and into the tissue, and wherein the photodetector is configured to receive the reflected light through the optical window. In some embodiments, the scan head further includes a second light source configured to transmit light at a second wavelength into the tissue. In some embodiments, the scan head further includes: an optical window, and a second light source, wherein the first light source is configured to transmit the light at the first wavelength through the optical window and into the tissue, wherein the second light source is configured to transmit light at a second wavelength through the optical window and into the tissue, and wherein the photodetector is configured to receive the reflected light through the optical window.

In some embodiments of the device, the diagnostic device is configured to be handheld. In some embodiments, the scan head further includes a mechano-transduction module configured to provide repetitive mechanical stress to the tissue. In some embodiments, the scan head includes a reflector panel configured to selectively control an amount of specular and diffuse light reflected to the photodetector. In some embodiments, the scan head is made from a material that includes medical-grade acrylonitrile butadiene styrene (ABS).

In some embodiments of the device, the first light source is a light-emitting diode (LED). In some embodiments, the first wavelength is approximately 760 nanometers (nm). In some embodiments, the first wavelength is approximately 850 nanometers (nm). In some embodiments, the scan head further includes a second light source configured to transmit light at a second wavelength into the tissue, wherein the first wavelength is approximately 760 nanometers (nm), and wherein the second wavelength is approximately 850 nm.

In some embodiments, the present invention provides a method of treating a tissue of a subject, wherein the tissue has a risk of ulceration. This method includes: determining a first physiological state of the tissue by obtaining a first sequence of NIR readings of the tissue during a first time interval while the subject is at rest; combining spatial information from the first sequence of NIR readings to find an oxygenated hemoglobin concentration parameter and a deoxygenated hemoglobin concentration parameter and a light-absorption parameter to characterize the first physiological state; applying a repetitive stress condition to the tissue for a second time interval; removing the repetitive stress condition that was applied to the tissue; determining a second physiological state of the tissue by obtaining a second sequence of NIR readings of the tissue during a third time interval while the subject is at rest; combining spatial information from the second sequence of NIR readings to find an oxygenated hemoglobin concentration parameter and a deoxygenated hemoglobin concentration parameter and a light-absorption parameter to characterize the second physiological state; comparing the first set of readings with the second set of NIR readings to determine a difference between the first and second physiological states of the tissue, wherein the oxyhemoglobin concentration in the arms and feet of ulcerated subjects is lower than oxyhemoglobin concentration in diabetics; characterizing a pattern of ulceration susceptibility by a time-delay interval required to minimize the difference between the first and second physiological states, wherein the time-delay interval is a time period of perfusion recovery and/or the absolute difference in oxyhemoglobin concentration with the subject at rest with the lowest level of oxyhemoglobin concentration during recovery, wherein the risk of ulceration is determined by comparing the difference between the first and second physiological states of the subject at two different anatomical sites of the subject; determining a ratio of oxyhemoglobin concentration at the two anatomical sites to generate a metric used to distinguish healthy tissue from tissue that is ulcerated or at risk of ulceration; determining a ratio of oxyhemoglobin concentration at the two anatomical sites via an absolute difference in oxyhemoglobin concentration with the subject at rest with a lowest level of oxyhemoglobin during recovery to generate a second metric for distinguishing between healthy tissue from ulcerated tissue or tissue at risk of ulceration. The strong signal indicates the ability to distinguish diabetics at lower and high risk. The pattern of ulceration susceptibility is characterized by the time delay interval required to minimize the difference between the physiological states, i.e., the time period of perfusion recovery and/or the absolute difference in oxyhemoglobin with the subject at rest with the lowest level of oxyhemoglobin during recovery. The risk of ulceration is determined by comparing the difference between the first and second physiological states of the subject at two different anatomical sites (e.g., the chest and leg of the subject). The metric used to distinguish healthy tissue from ulcerated or tissue at risk of ulceration is determined by generating a ratio of oxyhemoglobin at the two anatomical sites (e.g., the chest and foot of the subject). The ratio of oxyhemoglobin is referred to as perfusion index value. A second metric for distinguishing between healthy tissue from ulcerated or at risk to ulcerate is determined by generating a ratio of oxyhemoglobin at two anatomical sites via an absolute difference in oxyhemoglobin with the subject at rest with the lowest level of oxyhemoglobin during recovery. This ratio of oxyhemoglobin is referred to as a perfusion recovery index value. This method is applicable to where the tissue is a toe, a foot, a finger, an arm, a leg or any portion thereof.

In some embodiments, the present invention provides a method of applying a treatment to a tissue of a subject capable of assessing a risk to ulcerate, the method comprising:

(A) determining a first physiological state of the tissue by using a near infrared (NIR) imaging device to obtain a first sequence of NIR images of the tissue while the subject is at rest;

(B) applying a repetitive stress condition to the tissue for a predefined time interval;

(C) removing the repetitive stress condition applied to the tissue;

(C) determining a second physiological state of the tissue by using a NIR imaging device to obtaining a second sequence of NIR images of the tissue for a fixed time interval while the subject is at rest; and (D) comparing the first set of images with the second set of NIR images to determine a difference between the first and second physiological states of the tissue.

In some embodiments, the physiological state of the tissue is characterized by combining spatial information from the independent parameters: oxygenated and deoxygenated hemoglobin concentration and light absorption. Oxyhemoglobin in the arms and feet of ulcerated subjects is typically lower than oxyhemoglobin in diabetics. This provides the ability to distinguish diabetics at lower from those at high risk. In some embodiments, the pattern of ulceration susceptibility is characterized by the time delay interval required to minimize the difference between the physiological states, i.e., the time period of perfusion recovery and/or the absolute difference in oxyhemoglobin with the subject at rest with the lowest level of oxyhemoglobin during recovery. In some embodiments, the risk of ulceration is determined by comparing the difference between the first and second physiological states of the subject at two different anatomical sites (i.e., chest, and leg or foot of subject). In some embodiments, the metric used to distinguish healthy tissue from ulcerated or tissue at risk of ulceration is determined by generating a ratio of oxyhemoglobin at the two anatomical sites (i.e., chest, and leg or foot). The ratio of oxyhemoglobin is referred to as perfusion index value. In some embodiments, a second metric for distinguishing between healthy tissue from ulcerated or at risk to ulcerate is determined by generating a ratio of oxyhemoglobin at two anatomical sites via an absolute difference in oxyhemoglobin with the subject at rest with the lowest level of oxyhemoglobin during recovery. This ratio of oxyhemoglobin is referred to as a perfusion recovery index value. This method is applicable to where the tissue is a toe, a foot, a finger, an arm, a leg or any portion thereof.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first, " "second," and "third," etc., are used merely as labels, and are not intended to impose numerical requirements on their objects.

What is claimed is:

1. A diagnostic device for assessing ulceration risk in a tissue of a patient, the diagnostic device comprising:
   a hand-held housing, wherein the hand-held housing includes a user interface;
   an extension neck operatively coupled to the hand-held housing at a first end of the extension neck, wherein the extension neck has at least a first range of motion relative to the hand-held housing;
   a scan head operatively coupled to the extension neck at a second end of the extension neck, wherein the scan head has at least a second range of motion relative to the extension neck, and wherein the hand-held housing, the extension neck, and the scan head are arranged such that pressure is applied to the tissue of the patient from the scan head by a person holding the hand-held housing, and wherein the scan head includes:
      a light-emitting system configured to emit light at a selected wavelength of a predetermined set of wavelengths at a first time and to direct the emitted light into the tissue; and
      a photodetector configured to receive light reflected from the tissue and generate an electrical signal based on the received reflected light;
   a controller operatively coupled to the user interface and configured to control the light-emitting system and the photodetector; and
   a processor operatively coupled to the photodetector and the controller and configured to calculate regional-perfusion-index (RPI) data based at least in part on the electrical signal generated by the photodetector.

2. The diagnostic device of claim 1, wherein the scan head includes an optical window, wherein the light-emitting system is configured to transmit the emitted light through the optical window and into the tissue, and wherein the photodetector is configured to receive the reflected light through the optical window.

3. The diagnostic device of claim 1, wherein the scan head further includes an optical window that is textured on its skin-facing surface, and wherein the processor is configured to determine the RPI data as the patient presses the optical window against the tissue and moves the scan head across the tissue to provide pressure differences to different portions of the tissue over time.

4. The diagnostic device of claim 1, wherein the scan head further includes an optical window that includes a transverse groove on an outer surface, and wherein the processor is configured to determine the RPI data as the patient presses the optical window against the tissue and moves the scan head across the tissue to provide pressure differences to different portions of the tissue over time.

5. The diagnostic device of claim 1, wherein the scan head further includes an optical window that includes a transverse ridge on an outer surface, and wherein the processor is configured to determine the RPI data as the patient presses the optical window against the tissue and moves the scan head across the tissue to provide pressure differences to different portions of the tissue over time.

6. The diagnostic device of claim 1, wherein the diagnostic device is battery powered.

7. The diagnostic device of claim 1, wherein the scan head includes a mechano-transduction vibration module configured to provide repetitive mechanical stress to the tissue.

8. The diagnostic device of claim 1, wherein the scan head includes an optical window, wherein the light-emitting system is configured to transmit the emitted light through the optical window and into the tissue, wherein the photodetector is configured to receive the reflected light through the optical window, wherein the optical window includes at least a first raised surface area, and wherein the optical window is configured to provide repetitive mechanical stress to the tissue.

9. The diagnostic device of claim 1, wherein the scan head includes a reflector panel configured to selectively control an amount of specular and diffuse light reflected to the photodetector.

10. The diagnostic device of claim 1, wherein the user interface includes an organic light-emitting diode (OLED) display configured to provide adjustable optical power, to display remaining battery life, and to display the RPI data.

11. A method for assessing ulceration risk in a tissue, the method comprising:
    providing a diagnostic device, wherein the diagnostic device includes:
        a hand-held housing, wherein the hand-held housing includes a user interface,
        an extension neck operatively coupled to the hand-held housing at a first end of the extension neck, wherein the extension neck has at least a first range of motion relative to the hand-held housing,
        a scan head operatively coupled to the extension neck at a second end of the extension neck, wherein the scan head has at least a second range of motion relative to the extension neck, wherein the scan head includes a light-emitting system and a photodetector, and wherein the hand-held housing, the extension neck, and the scan head are arranged such that pressure is applied to the tissue of the patient from the scan head by a person holding the hand-held housing,
        a controller operatively coupled to the user interface and configured to control the light-emitting system and the photodetector, and
        a processor operatively coupled to the photodetector and the controller;
    rolling the scan head in a medial and lateral direction across the tissue while holding the hand-held housing;
    emitting light at a selected wavelength of a predetermined set of wavelengths from the light-emitting system at a first time and directing the emitted light into the tissue;
    receiving light reflected from the tissue at the photodetector and generating an electrical signal based on the received reflected light;
    calculating, via the processor, regional-perfusion-index (RPI) data based at least in part on the electrical signal; and
    displaying the RPI data via the user interface.

12. The method of claim 11, wherein the scan head further includes an optical window that is textured, the method further including pressing the optical window against the tissue and moving the scan head across the tissue to provide pressure differences to different portions of the tissue over time.

13. The method of claim 11, wherein the scan head further includes an optical window that has a transverse groove on an outer surface, the method further including pressing the optical window against the tissue and moving the scan head across the tissue to provide pressure differences to different portions of the tissue over time.

14. The method of claim 11, wherein the displaying includes indicating a concentration of deoxygenated hemoglobin (deoxy-Hb) and oxygenated hemoglobin (oxy-Hb) in blood flowing through the tissue.

15. The method of claim 11, wherein the scan head further includes a vibration transducer on an outer surface, the method further including pressing the vibration transducer against the tissue and moving the scan head across the tissue to provide pressure differences to different portions of the tissue over time.

16. The method of claim 11, further comprising providing a repetitive mechanical stress to the tissue.

17. The method of claim 11, wherein the rolling includes rolling the scan head in a medial and lateral direction across chest tissue and rolling the scan head in a medial and lateral direction across foot tissue, wherein the RPI data includes an RPI value that is equivalent to a first oxygenated hemoglobin value of the chest tissue divided by a second oxygenated hemoglobin value of the foot tissue.

18. An apparatus for assessing ulceration risk in a tissue, the apparatus comprising:
    a diagnostic device that includes a hand-held housing, a scan head, and means for pressing and rolling the scan head in a medial and lateral direction across the tissue while holding the hand-held housing, wherein the means for pressing and rolling the scan head has at least a first range of motion relative to the hand-held housing, wherein the scan head has at least a second range of motion relative to the means for pressing and rolling the scan head, and wherein the hand-held housing, the scan head, and the means for pressing and rolling the scan head are arranged such that pressure is applied to the tissue of the patient from the scan head by a person holding the hand-held housing;
    means for emitting light from the scan head at a selected wavelength of a predetermined set of wavelengths from the light-emitting system at a first time and directing the emitted light into the tissue;
    means for receiving light reflected from the tissue and for generating an electrical signal based on the received reflected light;
    means for controlling the means for emitting light and the means for receiving light;
    means for calculating regional-perfusion-index (RPI) data based at least in part on the electrical signal; and
    means for displaying the RPI data.

19. The apparatus of claim 18, further comprising:
    means, in the diagnostic device, for determining a first physiological state of the tissue by obtaining a first sequence of near-infrared (NIR) readings of the tissue during a first time interval while the subject is at rest;
    means for combining spatial information from the first sequence of NIR readings to find an oxygenated hemoglobin concentration parameter and a deoxygenated hemoglobin concentration parameter and a light-absorption parameter to characterize the first physiological state;
    means for applying a repetitive stress condition to the tissue for a second time interval;
    means for removing the repetitive stress condition that was applied to the tissue;

means, in the diagnostic device, for determining a second physiological state of the tissue by obtaining a second sequence of NIR readings of the tissue during a third time interval while the subject is at rest;

means for combining spatial information from the second sequence of NIR readings to find an oxygenated hemoglobin concentration parameter and a deoxygenated hemoglobin concentration parameter and a light-absorption parameter to characterize the second physiological state;

means for comparing the first set of readings with the second set of NIR readings to determine a difference between the first and second physiological states of the tissue, wherein the oxyhemoglobin concentration in the arms and feet of ulcerated subjects is lower than oxyhemoglobin concentration in diabetics;

means for characterizing a pattern of ulceration susceptibility by a time-delay interval required to minimize the difference between the first and second physiological states, wherein the time-delay interval is a time period of perfusion recovery and/or the absolute difference in oxyhemoglobin concentration with the subject at rest with the lowest level of oxyhemoglobin concentration during recovery, wherein the risk of ulceration is determined by comparing the difference between the first and second physiological states of the subject at two different anatomical sites of the subject;

means for determining a ratio of oxyhemoglobin concentration at the two different anatomical sites to generate a first metric used to distinguish healthy tissue from tissue that is ulcerated or at risk of ulceration; and means for determining a ratio of oxyhemoglobin concentration at the two different anatomical sites via an absolute difference in oxyhemoglobin concentration with the subject at rest with a lowest level of oxyhemoglobin during recovery to generate a second metric for distinguishing between healthy tissue from ulcerated tissue or tissue at risk of ulceration.

20. The apparatus of claim 18, wherein the scan head includes means for providing a repetitive mechanical stress to the tissue.

* * * * *